United States Patent
Han et al.

(10) Patent No.: US 9,522,952 B2
(45) Date of Patent: Dec. 20, 2016

(54) POLYPEPTIDE BINDING TO ANNEXIN A1 AND USE THEREOF

(71) Applicant: Samsung Electronics Co., Ltd., Suwon-si, Gyeonggi-do (KR)

(72) Inventors: Jieun Han, Gunpo-si (KR); Jung Min Kim, Seoul (KR); Jae Il Lee, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 31 days.

(21) Appl. No.: 14/482,959

(22) Filed: Sep. 10, 2014

(65) Prior Publication Data

US 2015/0086553 A1    Mar. 26, 2015

(30) Foreign Application Priority Data

Sep. 10, 2013  (KR) .................... 10-2013-0108686

(51) Int. Cl.
*C07K 16/00*    (2006.01)
*C07K 16/18*    (2006.01)
*G01N 33/574*   (2006.01)

(52) U.S. Cl.
CPC ............. *C07K 16/18* (2013.01); *G01N 33/574* (2013.01); *C07K 2317/622* (2013.01); *G01N 2333/4718* (2013.01); *G01N 2800/24* (2013.01)

(58) Field of Classification Search
None
See application file for complete search history.

(56) References Cited

U.S. PATENT DOCUMENTS

| 2002/0127225 | A1 | 9/2002 | Hillman et al. |
| 2009/0311245 | A1* | 12/2009 | Devy ............... C07K 16/40 424/130.1 |
| 2012/0034209 | A1 | 2/2012 | Perretti et al. |
| 2013/0108639 | A1 | 5/2013 | Lee |
| 2013/0156780 | A1 | 6/2013 | D'Acquisto et al. |

FOREIGN PATENT DOCUMENTS

| KR | 2013-0012936 A | 2/2003 |
| KR | 2003-0013112 A | 2/2013 |
| WO | WO 2011/154705 A1 | 12/2011 |

OTHER PUBLICATIONS

Rudikoff et al. (Proceedings of the National Academy of Sciences, 1982, 79:1979-1983).*
MacCallum et al. (Journal of Molecular Biology, 1996, 262:732-745).*
Casset et al. (Biochemical and Biophysical Research Communications, 2003, 307:198-205).*
Vajdos et al. (Journal of Molecular Biology, 2002, 320:415-428).*
Chen et al. (Journal of Molecular Biology, 1999, 293:865-881).*
Gerke et al., "Annexins: From Structure to Function," *Physiol. Rev.*, 82: 331-371 (2002).
Lim et al., "Annexin 1: the new face of an old molecule," *The FASEB Journal Review*, pp. 968-975 (2006).

* cited by examiner

*Primary Examiner* — Sean Aeder
(74) *Attorney, Agent, or Firm* — Leydig, Voit & Mayer, Ltd.

(57) ABSTRACT

A polypeptide binding to Annexin A1, an antagonist against Annexin A1 including the polypeptide, an anti-Annexin A1 antibody including the polypeptide or an antigen-binding fragment thereof, and methods of preventing, treating and/or diagnosing a disease, including administering the antagonist and/or the antibody or an antigen-binding fragment thereof to a subject.

8 Claims, 10 Drawing Sheets

FIG. 5

FIG. 10
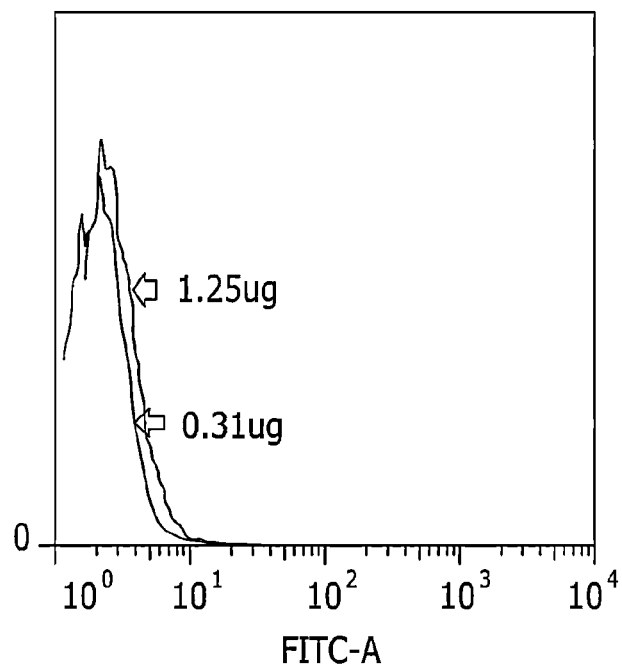
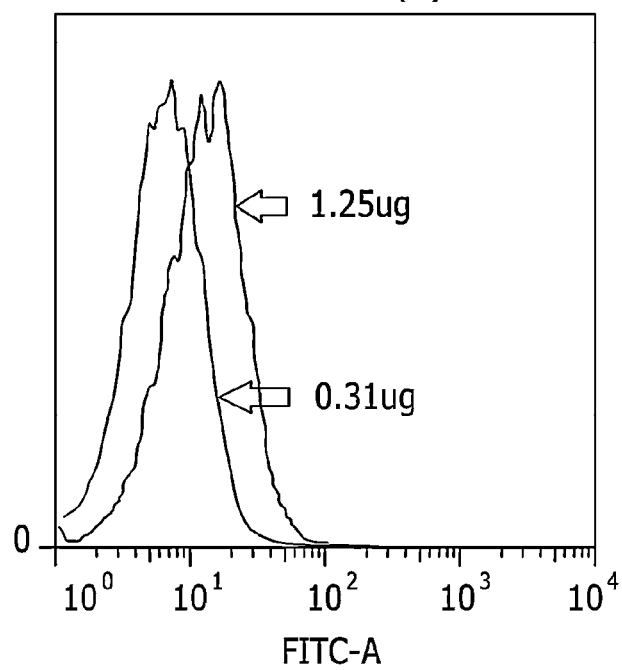

```
                        SEQUENCE LISTING

<160> NUMBER OF SEQ ID NOS: 155

<210> SEQ ID NO 1
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 1

Asn Tyr Ala Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 2

Asp Tyr Ser Met Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 3

Gly Tyr Ser Met Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 4

Asp Tyr Ala Met Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 5

Gly Tyr Ala Met Ser
1               5

<210> SEQ ID NO 6
<211> LENGTH: 5
<212> TYPE: PRT
<213> ORGANISM: Artificial Sequence
<220> FEATURE:
```

```
<223> OTHER INFORMATION: Synthetic (CDR-H1 of Anti-Annexin A1 antibody)

<400> SEQUENCE: 6

Ser Tyr Ala Met Ser
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 7

Asn Tyr Ser Met Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 8

Gly Tyr Tyr Met Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 9

Ser Tyr Ser Met Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 10

Asp Tyr Ser Met Ser
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)

<400> SEQUENCE: 11

Ser Tyr Tyr Met Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)
```

```
<400> SEQUENCE: 12

Ala Ile Ser Pro Gly Asp Ser Asn Thr
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 13

Gly Ile Tyr Pro Asn Ser Gly Ser Asn Thr
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 14

Gly Ile Tyr Pro Ser Gly Gly Asn Thr
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 15

Ala Ile Tyr Pro Gly Gly Gly Ser Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 16

Gly Ile Tyr Ser Gly Asp Ser Ser Lys
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 17

Gly Ile Ser Ser Asp Asp Gly Ser Lys Tyr
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)
```

```
<400> SEQUENCE: 18

Gly Ile Tyr Pro Ser Ser Ser Ser Lys
1               5

<210> SEQ ID NO 19
<211> LENGTH: 10
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 19

Gly Ile Ser Ser Asp Asn Ser Ser Lys Tyr
1               5                   10

<210> SEQ ID NO 20
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 20

Gly Ile Tyr Tyr Gly Asp Gly Ser Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 21

Ala Ile Tyr Pro Gly Asn Gly Ser Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 22

Gly Ile Tyr Pro Gly Gly Gly Ser Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 23

Gly Ile Tyr Pro Gly Gly Ser Ser Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 24
```

```
Ala Ile Tyr Pro Asp Gly Gly Ser Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 25

Gly Ile Tyr Pro Ser Asp Gly Asn Ile
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 26

Ala Ile Tyr Pro Ser Asn Gly Ser Lys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 27

Gly Ile Ser Ser Asp Gly Gly Asn Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 28

Ser Ile Ser Pro Ser Gly Ser Ser Ile
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 29

Gly Ile Ser Tyr Gly Gly Gly Asn Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 30
```

Ser Ile Ser Ser Asn Ser Gly Asn Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 31

Gly Ile Ser Pro Gly Ser Gly Ser Ile
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 32

Val Ile Ser Pro Asp Ser Ser Asn Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 33

Ser Ile Ser Pro Asp Gly Gly Asn Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 34

Gly Ile Ser Pro Asp Gly Gly Ser Ile
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 35

Gly Ile Ser Pro Asp Asp Gly Ser Ile
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 36

Leu Ile Ser Pro Gly Ser Gly Ser Ile

```
<210> SEQ ID NO 37
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 37

Gly Ile Ser Pro Asn Gly Gly Ser Ile
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 38

Ala Ile Ser Ser Ser Gly Gly Ser Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 39

Ser Ile Ser Pro Ser Ser Gly Ser Ile
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 40

Leu Ile Ser Pro Asp Ser Ser Ser Ile
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 41

Ser Ile Ser Tyr Gly Asn Ser Asn Lys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic (CDR-H2 of Anti-Annexin A1 antibody)

<400> SEQUENCE: 42

Ala Ile Ser Ser Asp Gly Gly Ser Thr
1               5
```

<210> SEQ ID NO 43
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 43

Arg Met Thr Lys Arg Phe Asp Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 44

Arg Arg Pro Thr Leu Phe Asp Tyr
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 45

Arg Lys Pro Thr Ile Phe Asp Tyr
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 46

Arg Arg Leu Gln Ile Phe Asp Tyr
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 47

Arg Ser Leu Ser Ile Phe Asp Tyr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 48

Ala Arg Thr Leu Thr Ile Phe Asp Tyr
1               5

<210> SEQ ID NO 49
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 49

Lys Arg Leu Ala Leu Phe Asp Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 50

Arg Arg Ile Ser Leu Phe Asp Tyr
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 51

Arg Arg Ala Thr Leu Phe Asp Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 52

Lys Gly Leu Ser Leu Phe Asp Tyr
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 53

Arg Arg Leu Thr Ile Phe Asp Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 54

Lys Arg Pro Ser Arg Phe Asp Tyr
1               5

```
<210> SEQ ID NO 55
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 55

Lys Arg Pro Thr Leu Phe Asp Tyr
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 56

Lys Arg Ile Thr Leu Phe Asp Tyr
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 57

Lys Asn Lys Ala Pro Phe Asp Tyr
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 58

Arg Arg Ala Ile Pro Phe Asp Tyr
1               5

<210> SEQ ID NO 59
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 59

Lys Gly Ser Pro Gly Phe Asp Tyr
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 60

Lys Arg Leu Gly Ser Phe Asp Tyr
1               5

<210> SEQ ID NO 61
```

```
<211> LENGTH: 19
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 61

Lys Ala Thr Leu Gly Met Asp His Ile His Ala Tyr Ser Ala Tyr Gly
1               5                   10                  15

Met Asp Val

<210> SEQ ID NO 62
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 62

Arg Arg Ile His Pro Phe Asp Tyr
1               5

<210> SEQ ID NO 63
<211> LENGTH: 19
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 63

Lys Val Thr Gly Thr Cys Gly Pro Arg Ser Cys Tyr Tyr Tyr Asp Ala
1               5                   10                  15

Met Asp Val

<210> SEQ ID NO 64
<211> LENGTH: 8
<212> TYPE: PRT
<213> ORGANISM: Artificial Sequence
<220> FEATURE:
<223> OTHER INFORMATION: Synthetic (DR-H3 of Anti-Annexin A1 antibody)

<400> SEQUENCE: 64

Lys Arg Thr Thr Leu Phe Asp Tyr
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 65

Arg Arg Ser Ser Leu Phe Asp Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 66

Arg Arg Val Gly Leu Phe Asp Tyr
1               5
```

<210> SEQ ID NO 67
<211> LENGTH: 19
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 67

Arg Ser Ile Ser Gly Arg Gln Tyr Ala Asn Pro Ser Tyr Asp Asp Ala
1               5                   10                  15

Met Asp Val

<210> SEQ ID NO 68
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 68

Lys Arg Ala Ala Leu Phe Asp Tyr
1               5

<210> SEQ ID NO 69
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 69

Arg Arg Gly Asn Leu Phe Asp Tyr
1               5

<210> SEQ ID NO 70
<211> LENGTH: 13
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 70

Lys Gly Gly Pro Ala Arg Arg Ala Ser Thr Phe Asp Tyr
1               5                   10

<210> SEQ ID NO 71
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 71

Lys Arg Asn Trp Thr Phe Asp Tyr
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 72

Lys Arg Ala Thr Val Phe Asp Tyr

```
1               5
```

<210> SEQ ID NO 73
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 73

```
Arg Ala Pro Gly Pro Phe Asn Tyr
1               5
```

<210> SEQ ID NO 74
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)

<400> SEQUENCE: 74

```
Arg Arg Gly Ala Leu Phe Asp Tyr
1               5
```

<210> SEQ ID NO 75
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 75

```
Ser Gly Ser Ser Ser Asn Ile Gly Ser Asn Asp Val Thr
1               5                   10
```

<210> SEQ ID NO 76
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 76

```
Thr Gly Ser Ser Ser Asn Ile Gly Ser Asn Ser Val Asn
1               5                   10
```

<210> SEQ ID NO 77
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 77

```
Ser Gly Ser Ser Ser Asn Ile Gly Asn Asn Asp Val Asn
1               5                   10
```

<210> SEQ ID NO 78
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 78

```
Thr Gly Ser Ser Ser Asn Ile Gly Ser Asn Asn Val Thr
1               5                   10
```

```
<210> SEQ ID NO 79
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 79

Ser Gly Ser Ser Ser Asn Ile Gly Ser Asn Ala Val Thr
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 80

Ser Gly Ser Ser Ser Asn Ile Gly Ser Asn Asn Val Thr
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 81

Ser Gly Ser Ser Ser Asn Ile Gly Asn Asn Ala Val Asn
1               5                   10

<210> SEQ ID NO 82
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 82

Thr Gly Ser Ser Ser Asn Ile Gly Ser Asn Ser Val Ser
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 83

Ser Gly Ser Ser Ser Asn Ile Gly Asn Asn Asp Val
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 84

Thr Gly Ser Ser Ser Asn Ile Gly Asn Asn Asp Val Asn
1               5                   10
```

<210> SEQ ID NO 85
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 85

Thr Gly Ser Ser Ser Asn Ile Gly Asn Asn Thr Val Ser
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 86

Thr Gly Ser Ser Ser Asn Ile Gly Ser Asn Ala Val Ser
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 87

Ser Gly Ser Ser Phe Asn Ile Gly Ser Asn Asp Val Ser
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 88

Thr Gly Thr Ser Ser Asn Ile Gly Ser Asn Tyr Val Ser
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 89

Thr Gly Ser Ser Ser Asn Ile Gly Asn Asn Asp Val Ser
1               5                   10

<210> SEQ ID NO 90
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 90

Ser Gly Ser Ser Ser Asn Ile Gly Ser Asn Ala Val Ser
1               5                   10

```
<210> SEQ ID NO 91
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 91

Thr Gly Ser Ser Ser Asn Ile Gly Ser Asn Asp Val Ser
1               5                   10

<210> SEQ ID NO 92
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 92

Thr Gly Ser Ser Ser Asn Ile Gly Asn Asn Ser Val Thr
1               5                   10

<210> SEQ ID NO 93
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 93

Ser Gly Ser Ser Ser Asn Ile Gly Ser Asn Asp Val Ser
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)

<400> SEQUENCE: 94

Thr Gly Ser Ser Ser Asn Ile Gly Ile Asn Asp Val Ser
1               5                   10

<210> SEQ ID NO 95
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 95

Asp Asn Ser Lys
1

<210> SEQ ID NO 96
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 96

Ser Asp Ser His
1

<210> SEQ ID NO 97
```

```
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 97

Ser Asn Ser His
1

<210> SEQ ID NO 98
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 98

Ser Asn Ser Gln
1

<210> SEQ ID NO 99
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 99

Ser Asp Asn His
1

<210> SEQ ID NO 100
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 100

Ala Asp Ser Asn
1

<210> SEQ ID NO 101
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 101

Tyr Asn Ser Gln
1

<210> SEQ ID NO 102
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 102

Ala Gly Asn His
1

<210> SEQ ID NO 103
<211> LENGTH: 4
```

```
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 103

Ala Asn Ser Asn
1

<210> SEQ ID NO 104
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 104

Ser Asp Asn Gln
1

<210> SEQ ID NO 105
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 105

Tyr Asn Ser His
1

<210> SEQ ID NO 106
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 106

Asp Asn Ser Gln
1

<210> SEQ ID NO 107
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 107

Asp Ser Gln Arg
1

<210> SEQ ID NO 108
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 108

Tyr Asp Asn Gln
1

<210> SEQ ID NO 109
<211> LENGTH: 4
<212> TYPE: PRT
```

```
<213> ORGANISM: Artificial Sequence
<220> FEATURE:
<223> OTHER INFORMATION: Synthetic (CDR-L2 of Anti-Annexin A1 antibody)

<400> SEQUENCE: 109

Tyr Asp Ser Asn
1

<210> SEQ ID NO 110
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 110

Asp Asp Ser Asn
1

<210> SEQ ID NO 111
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 111

Asp Asn Ser Lys
1

<210> SEQ ID NO 112
<211> LENGTH: 4
<212> TYPE: PRT
<213> ORGANISM: Artificial Sequence
<220> FEATURE:
<223> OTHER INFORMATION: Synthetic (CDR-L2 of Anti-Annexin A1 antibody)

<400> SEQUENCE: 112

Ala Asp Asn Asn
1

<210> SEQ ID NO 113
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 113

Gly Thr Trp Asp Asp Ser Leu Asn Gly
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 114

Ala Thr Trp Asp Asp Ser Leu Asn Gly
1               5

<210> SEQ ID NO 115
<211> LENGTH: 9
<212> TYPE: PRT
<213> ORGANISM: Artificial Sequence
```

```
<220> FEATURE:
<223> OTHER INFORMATION: Synthetic (CDR-L3 of Anti-Annexin A1 antibody)

<400> SEQUENCE: 115

Gly Ser Trp Asp Tyr Ser Leu Ser Ala
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 116

Gly Thr Trp Asp Tyr Ser Leu Ser Gly
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 117

Gly Ala Trp Asp Tyr Ser Leu Ser Gly
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 118

Gly Ala Trp Asp Tyr Ser Leu Asn Ala
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 119

Gly Thr Trp Asp Asp Ser Leu Ser Gly
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 120

Gly Thr Trp Asp Asp Ser Leu Ser Ala
1               5

<210> SEQ ID NO 121
<211> LENGTH: 9
<212> TYPE: PRT
<213> ORGANISM: Artificial Sequence
<220> FEATURE:
```

```
<223> OTHER INFORMATION: Synthetic (CDR-L3 of Anti-Annexin A1 antibody)

<400> SEQUENCE: 121

Ala Thr Trp Asp Asp Ser Leu Asn Ala
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 122

Gly Ala Trp Asp Tyr Ser Leu Asn Gly
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 123

Gly Ala Trp Asp Asp Ser Leu Asn Ala
1               5

<210> SEQ ID NO 124
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 124

Gly Ser Trp Asp Ser Ser Leu Ser Ala
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 125

Ala Ala Trp Asp Asp Ser Leu Asn Ala
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 126

Gly Ala Trp Asp Ser Ser Leu Asn Ala
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)
```

<400> SEQUENCE: 127

Ala Thr Trp Asp Ser Ser Leu Asn Gly
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 128

Ala Ala Trp Asp Ala Ser Leu Ser Ala
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 129

Gly Ser Trp Asp Ala Ser Leu Ser Ala
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 130

Gly Ala Trp Asp Ala Ser Leu Ser Ala
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 131

Gly Ala Trp Asp Asp Ser Leu Ser Gly
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 132

Gly Ser Trp Asp Ala Ser Leu Asn Gly
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

```
<400> SEQUENCE: 133

Gly Ser Trp Asp Asp Ser Leu Ser Gly
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 134

Gly Thr Trp Asp Ser Ser Leu Ser Gly
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 135

Ala Ala Cys Asp Asp Asn Leu Asn Asp
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)

<400> SEQUENCE: 136

Gly Ser Trp Asp Asp Ser Leu Ser Ala
1               5

<210> SEQ ID NO 137
<211> LENGTH: 243
<212> TYPE: PRT
<213> ORGANISM: Artificial Sequence
<220> FEATURE:
<223> OTHER INFORMATION: Synthetic (Anti-Annexin A1 scFv N32)

<400> SEQUENCE: 137

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Gly Ile Tyr Pro Asn Ser Gly Ser Asn Thr Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Pro Thr Leu Phe Asp Tyr Trp Gly Gln Gly Thr Leu
            100                 105                 110

Val Thr Val Gly Ser Gly Gly Gly Gly Ser Gly Gly Gly Gly Ser Gly
        115                 120                 125

Gly Gly Gly Ser Gln Ser Val Leu Thr Gln Pro Pro Ser Ala Ser Gly
```

```
                130               135               140
Thr Pro Gly Gln Arg Val Thr Ile Ser Cys Thr Gly Ser Ser Ser Asn
145                 150                 155                 160

Ile Gly Ser Asn Ser Val Asn Trp Tyr Gln Gln Leu Pro Gly Thr Ala
                165                 170                 175

Pro Lys Leu Leu Ile Tyr Ser Asp Ser His Arg Pro Ser Gly Val Pro
                180                 185                 190

Asp Arg Phe Ser Gly Ser Lys Ser Gly Thr Ser Ala Ser Leu Ala Ile
                195                 200                 205

Ser Gly Leu Gln Ser Glu Asp Glu Ala Asp Tyr Tyr Cys Ala Thr Trp
                210                 215                 220

Asp Asp Ser Leu Asn Gly Tyr Val Phe Gly Gly Gly Thr Lys Leu Thr
225                 230                 235                 240

Val Leu Gly

<210> SEQ ID NO 138
<211> LENGTH: 242
<212> TYPE: PRT
<213> ORGANISM: Artificial Sequence
<220> FEATURE:
<223> OTHER INFORMATION: Synthetic (Anti-Annexin A1 scFv N34)

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Ala Met Ser Trp Val Arg Gln Ala Pro Gly Lys Gly Leu Glu Trp Val
            35                  40                  45

Ser Ala Ile Tyr Pro Gly Gly Ser Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Gln Ile Phe Asp Tyr Trp Gly Gln Gly Thr Leu Val
                100                 105                 110

Thr Val Ser Ser Gly Gly Gly Gly Ser Gly Gly Gly Gly Ser Gly Gly
            115                 120                 125

Gly Gly Ser Gln Ser Val Leu Thr Gln Pro Pro Ser Ala Ser Gly Thr
        130                 135                 140

Pro Gly Gln Arg Val Thr Ile Ser Cys Thr Gly Ser Ser Ser Asn Ile
145                 150                 155                 160

Gly Ser Asn Asn Val Thr Trp Tyr Gln Gln Leu Pro Gly Thr Ala Pro
                165                 170                 175

Lys Leu Leu Ile Tyr Ser Asp Ser His Arg Pro Ser Gly Val Pro Asp
            180                 185                 190

Arg Phe Ser Gly Ser Lys Ser Gly Thr Ser Ala Ser Leu Ala Ile Ser
                195                 200                 205

Gly Leu Gln Ser Glu Asp Glu Ala Asp Tyr Tyr Cys Gly Ser Trp Asp
        210                 215                 220

Tyr Ser Leu Ser Ala Tyr Val Phe Gly Gly Gly Thr Lys Leu Thr Val
225                 230                 235                 240

Leu Gly
```

<210> SEQ ID NO 139
<211> LENGTH: 242
<212> TYPE: PRT
<213> ORGANISM: Artificial Sequence
<220> FEATURE:
<223> OTHER INFORMATION: Synthetic (Anti-Annexin A1 scFv N314)

<400> SEQUENCE: 139

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Ala Met Ser Trp Val Arg Gln Ala Pro Gly Lys Gly Leu Glu Trp Val
        35                  40                  45

Ser Gly Ile Tyr Pro Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Leu Thr Ile Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Gln Arg Val Thr Ile Ser Cys Ser Gly Ser Ser Ser Asn Ile
145                 150                 155                 160

Gly Asn Asn Asp Val Thr Trp Tyr Gln Gln Leu Pro Gly Thr Ala Pro
                165                 170                 175

Lys Leu Leu Ile Tyr Ser Asp Ser His Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Thr Trp Asp
    210                 215                 220

Asp Ser Leu Ser Gly Tyr Val Phe Gly Gly Gly Thr Lys Leu Thr Val
225                 230                 235                 240

Leu Gly
```

<210> SEQ ID NO 140
<211> LENGTH: 242
<212> TYPE: PRT
<213> ORGANISM: Artificial Sequence
<220> FEATURE:
<223> OTHER INFORMATION: Synthetic (Anti-Annexin A1 scFv N43)

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Gly Trp Val Arg Gln Ala Pro Gly Arg Gly Leu Glu Trp Val
        35                  40                  45

Ser Gly Ile Tyr Pro Ser Gly Gly Asn Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Pro Ser Arg Phe Asp Tyr Trp Gly Gln Gly Thr Leu Val
            100                 105                 110

Ala Val Ser Ser Gly Gly Gly Gly Ser Gly Gly Gly Ser Gly Gly
            115                 120                 125

Gly Gly Ser Gln Ser Val Leu Thr Gln Pro Pro Ser Ala Ser Gly Thr
130                 135                 140

Pro Gly Gln Arg Val Thr Ile Ser Cys Thr Gly Ser Ser Ser Asn Ile
145                 150                 155                 160

Gly Asn Asn Asp Val Asn Trp Tyr Gln Gln Leu Pro Gly Thr Ala Pro
                165                 170                 175

Lys Leu Leu Ile Tyr Ser Asn Ser His Arg Pro Ser Gly Val Pro Asp
                180                 185                 190

Arg Phe Ser Gly Ser Lys Ser Gly Thr Ser Ala Ser Leu Ala Ile Ser
            195                 200                 205

Gly Leu Arg Ser Glu Asp Glu Ala Asp Tyr Tyr Cys Gly Thr Trp Asp
210                 215                 220

Asp Ser Leu Asn Gly Tyr Val Phe Gly Gly Gly Thr Lys Leu Thr Val
225                 230                 235                 240

Leu Gly

<210> SEQ ID NO 141
<211> LENGTH: 242
<212> TYPE: PRT
<213> ORGANISM: Artificial Sequence
<220> FEATURE:
<223> OTHER INFORMATION: Synthetic (Anti-Annexin A1 scFv F2)

<400> SEQUENCE: 141

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
                 20                  25                  30

Ser Met Ser Trp Val Arg Gln Ala Pro Gly Lys Gly Leu Glu Trp Val
             35                  40                  45

Ser Gly Ile Ser Ser Asp Gly Gly Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Ala Ile Pro Phe Asp Tyr Trp Gly Gln Gly Thr Leu Val
            100                 105                 110

Thr Val Ser Ser Gly Gly Gly Gly Ser Gly Gly Gly Ser Gly Gly
            115                 120                 125

Gly Gly Ser Gln Ser Val Leu Thr His Pro Pro Ser Ala Ser Gly Thr
130                 135                 140

Pro Gly Gln Arg Val Thr Ile Ser Cys Thr Gly Ser Ser Ser Asn Ile
145                 150                 155                 160

Gly Ser Asn Ala Val Ser Trp Tyr Gln Gln Leu Pro Gly Thr Ala Pro
                165                 170                 175

Lys Leu Leu Ile Tyr Tyr Asn Ser Gln Arg Pro Ser Gly Val Pro Asp
```

```
                    180                 185                 190
Arg Phe Ser Gly Ser Lys Ser Gly Thr Ser Ala Ser Leu Ala Ile Ser
                195                 200                 205

Gly Leu Arg Ser Glu Asp Glu Ala Asp Tyr Tyr Cys Gly Ala Trp Asp
        210                 215                 220

Asp Ser Leu Asn Ala Tyr Val Phe Gly Gly Gly Thr Lys Leu Thr Val
225                 230                 235                 240

Leu Gly

<210> SEQ ID NO 142
<211> LENGTH: 242
<212> TYPE: PRT
<213> ORGANISM: Artificial Sequence
<220> FEATURE:
<223> OTHER INFORMATION: Synthetic (Anti-Annexin A1 scFv F4)

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Tyr Met Ser Trp Val Arg Gln Ala Pro Gly Lys Gly Leu Glu Trp Val
        35                  40                  45

Ser Ser Ile Ser Pro Ser Gly Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Pro Gly Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Val Leu Thr Gln Pro Pro Ser Ala Ser Gly Ala
    130                 135                 140

Pro Gly Gln Arg Val Thr Ile Ser Cys Ser Gly Ser Ser Phe Asn Ile
145                 150                 155                 160

Gly Ser Asn Asp Val Ser Trp Tyr Gln Gln Leu Pro Gly Thr Ala Pro
                165                 170                 175

Lys Leu Leu Ile Tyr Ser Asp Ser His Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Gln Ser Glu Asp Glu Ala Asp Tyr Tyr Cys Gly Ser Trp Asp
    210                 215                 220

Tyr Ser Leu Ser Ala Tyr Val Phe Gly Gly Gly Thr Lys Leu Thr Val
225                 230                 235                 240

Leu Gly

<210> SEQ ID NO 143
<211> LENGTH: 242
<212> TYPE: PRT
<213> ORGANISM: Artificial Sequence
<220> FEATURE:
<223> OTHER INFORMATION: Synthetic (Anti-Annexin A1 scFv F5)

<400> SEQUENCE: 143
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Gly Ile Ser Tyr Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Leu Gly Ser Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Gln Ser Val Leu Thr Gln Pro Pro Ser Ala Ser Gly Thr
    130                 135                 140

Pro Gly Arg Arg Val Thr Ile Ser Cys Thr Gly Thr Ser Ser Asn Ile
145                 150                 155                 160

Gly Ser Asn Tyr Val Ser Trp Tyr Arg Gln Leu Pro Gly Thr Ala Pro
                165                 170                 175

Lys Leu Leu Ile Tyr Ala Gly Asn His Arg Pro Ser Gly Val Pro Asp
            180                 185                 190

Arg Phe Ser Gly Ser Lys Ser Gly Thr Ser Ala Ser Leu Ala Ile Ser
        195                 200                 205

Gly Leu Arg Ser Glu Asp Glu Ala Asp Tyr Tyr Cys Gly Ser Trp Asp
    210                 215                 220

Ser Ser Leu Ser Ala Tyr Val Phe Gly Gly Gly Thr Lys Leu Thr Val
225                 230                 235                 240

Leu Gly

<210> SEQ ID NO 144
<211> LENGTH: 253
<212> TYPE: PRT
<213> ORGANISM: Artificial Sequence
<220> FEATURE:
<223> OTHER INFORMATION: Synthetic (Anti-Annexin A1 scFv F6)

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ser Ile Ser Ser Asn Ser Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Thr Leu Gly Met Asp His Ile His Ala Tyr Ser Ala Tyr
            100                 105                 110
```

```
Gly Met Asp Val Trp Gly Gln Gly Thr Leu Val Thr Val Ser Ser Gly
            115                 120                 125
Gly Gly Gly Ser Gly Gly Gly Ser Gly Gly Gly Ser Gln Ser
        130                 135                 140
Val Leu Thr Gln Pro Pro Ser Ala Ser Gly Thr Pro Gly Gln Arg Ala
145                 150                 155                 160
Thr Ile Ser Cys Thr Gly Ser Ser Asn Ile Gly Ser Asn Ser Val
            165                 170                 175
Ser Trp Tyr Gln Gln Leu Pro Gly Thr Ala Pro Lys Leu Leu Ile Tyr
            180                 185                 190
Ala Asn Ser Asn Arg Pro Ser Gly Val Pro Asp Arg Phe Ser Gly Ser
            195                 200                 205
Lys Ser Gly Thr Ser Ala Ser Leu Ala Ile Ser Gly Leu Arg Ser Glu
            210                 215                 220
Asp Glu Ala Asp Tyr Tyr Cys Ala Ala Trp Asp Asp Ser Leu Asn Ala
225                 230                 235                 240
Tyr Val Phe Gly Gly Gly Thr Lys Leu Thr Val Leu Gly
                245                 250
```

```
<210> SEQ ID NO 145
<211> LENGTH: 242
<212> TYPE: PRT
<213> ORGANISM: Artificial Sequence
<220> FEATURE:
<223> OTHER INFORMATION: Synthetic (Anti-Annexin A1 scFv F8)

<400> SEQUENCE: 145
```

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ser Met Ser Trp Val Arg Gln Ala Pro Gly Lys Gly Leu Glu Trp Val
            35                  40                  45
Ser Gly Ile Ser Pro Gly Ser Gly Ser Ile Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Ile His Pro Phe Asp Tyr Trp Gly Gln Gly Thr Leu Val
            100                 105                 110
Ala Val Ser Ser Gly Gly Gly Gly Ser Gly Gly Gly Gly Ser Gly Gly
            115                 120                 125
Gly Gly Ser Gln Ser Val Leu Thr Gln Pro Pro Ser Ala Ser Gly Thr
        130                 135                 140
Pro Gly Gln Arg Val Thr Ile Ser Cys Thr Gly Ser Ser Ser Asn Ile
145                 150                 155                 160
Gly Asn Asn Asp Val Ser Trp Tyr Gln Gln Leu Pro Gly Thr Ala Pro
                165                 170                 175
Lys Leu Leu Ile Tyr Ser Asp Asn Gln Arg Pro Ser Gly Val Pro Gly
            180                 185                 190
Arg Phe Ser Gly Ser Lys Ser Gly Thr Ser Ala Ser Leu Ala Ile Ser
            195                 200                 205
Gly Leu Arg Ser Glu Asp Glu Ala Asp Tyr Tyr Cys Gly Ala Trp Asp
        210                 215                 220
```

Ser Ser Leu Asn Ala Tyr Val Phe Gly Gly Gly Thr Lys Leu Thr Val
225                 230                 235                 240

Leu Gly

<210> SEQ ID NO 146
<211> LENGTH: 253
<212> TYPE: PRT
<213> ORGANISM: Artificial Sequence
<220> FEATURE:
<223> OTHER INFORMATION: Synthetic (Anti-Annexin A1 scFv F10)

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ser Met Ser Trp Val Arg Gln Ala Pro Gly Lys Gly Leu Glu Trp Val
        35                  40                  45

Ser Val Ile Ser Pro Asp Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Gly Thr Cys Gly Pro Arg Ser Cys Tyr Tyr Tyr Asp
            100                 105                 110

Ala Met Asp Val Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Ser Gly Ser Ser Asn Ile Gly Ser Asn Ala Val
                165                 170                 175

Ser Trp Tyr Gln Gln Leu Pro Gly Thr Ala Pro Lys Leu Leu Ile Tyr
            180                 185                 190

Tyr Asn Ser His Arg Pro Ser Gly Val Pro Asp Arg Phe Ser Gly Pro
        195                 200                 205

Lys Ser Gly Thr Ser Ala Ser Leu Ala Ile Ser Gly Leu Arg Ser Glu
    210                 215                 220

Asp Glu Ala Asp Tyr Tyr Cys Ala Thr Trp Asp Ser Ser Leu Asn Gly
225                 230                 235                 240

Tyr Val Phe Gly Gly Gly Thr Lys Leu Thr Val Leu Gly
                245                 250

<210> SEQ ID NO 147
<211> LENGTH: 5
<212> TYPE: PRT
<213> ORGANISM: Artificial Sequence
<220> FEATURE:
<223> OTHER INFORMATION: Synthetic (CDR-H1 of Anti-Annexin A1 antibody)
<220> FEATURE:
<221> NAME/KEY: VARIANT
<222> LOCATION: (1)..(1)
<223> OTHER INFORMATION: Xaa is Asn(N), Gly(G), Asp(D), or Ser(S)
<220> FEATURE:
<221> NAME/KEY: VARIANT
<222> LOCATION: (3)..(3)
<223> OTHER INFORMATION: Xaa is Ala(A), Ser(S), or Tyr(Y)

```
<400> SEQUENCE: 147

Xaa Tyr Xaa Met Ser
1               5

<210> SEQ ID NO 148
<211> LENGTH: 8
<212> TYPE: PRT
<213> ORGANISM: Artificial Sequence
<220> FEATURE:
<223> OTHER INFORMATION: Synthetic (CDR-H3 of Anti-Annexin A1 antibody)
<220> FEATURE:
<221> NAME/KEY: VARIANT
<222> LOCATION: (1)..(1)
<223> OTHER INFORMATION: Xaa is Arg(R) or Lys(K)
<220> FEATURE:
<221> NAME/KEY: VARIANT
<222> LOCATION: (2)..(2)
<223> OTHER INFORMATION: Xaa is Arg(R), Gly(G), Ala(A), Met(M), Lys(K),
      Ser(S), or Asn(N)
<220> FEATURE:
<221> NAME/KEY: VARIANT
<222> LOCATION: (3)..(3)
<223> OTHER INFORMATION: Xaa is Ala(A), Ser(S), Leu(L), Ile(I), Thr(T),
      Val(V), Gly(G), Asn(N), Pro(P), or Lys(K)
<220> FEATURE:
<221> NAME/KEY: VARIANT
<222> LOCATION: (4)..(4)
<223> OTHER INFORMATION: Xaa is Ile(I), Pro(P), Gly(G), His(H), Thr(T),
      Ser(S), Ala(A), Asn(N), Trp(W), Lys(K), or Gln(Q)
<220> FEATURE:
<221> NAME/KEY: VARIANT
<222> LOCATION: (5)..(5)
<223> OTHER INFORMATION: Xaa Arg(R), Leu(L), Ile(I), Pro(P), Gly(G),
      Ser(S), Thr(T), or Val(V)

<400> SEQUENCE: 148

Xaa Xaa Xaa Xaa Xaa Phe Asp Tyr
1               5

<210> SEQ ID NO 149
<211> LENGTH: 13
<212> TYPE: PRT
<213> ORGANISM: Artificial Sequence
<220> FEATURE:
<223> OTHER INFORMATION: Synthetic (CDR-L1 of Anti-Annexin A1 antibody)
<220> FEATURE:
<221> NAME/KEY: VARIANT
<222> LOCATION: (1)..(1)
<223> OTHER INFORMATION: Xaa is Ser(S) or Thr(T)
<220> FEATURE:
<221> NAME/KEY: VARIANT
<222> LOCATION: (3)..(3)
<223> OTHER INFORMATION: Xaa is Ser(S) or Thr(T)
<220> FEATURE:
<221> NAME/KEY: VARIANT
<222> LOCATION: (5)..(5)
<223> OTHER INFORMATION: Xaa is Ser(S) or Phe(F)
<220> FEATURE:
<221> NAME/KEY: VARIANT
<222> LOCATION: (9)..(9)
<223> OTHER INFORMATION: Xaa is Ser(S), Asn(N), or Ile(I)
<220> FEATURE:
<221> NAME/KEY: VARIANT
<222> LOCATION: (11)..(11)
<223> OTHER INFORMATION: Xaa is Asp(D), Ser(S), Asn(N), Ala(A), Thr(T),
      or Tyr(Y)
<220> FEATURE:
<221> NAME/KEY: VARIANT
<222> LOCATION: (13)..(13)
<223> OTHER INFORMATION: Xaa is Thr(T), Asn(N), or Ser(S)

<400> SEQUENCE: 149

Xaa Gly Xaa Ser Xaa Asn Ile Gly Xaa Asn Xaa Val Xaa
1               5                   10
```

```
<210> SEQ ID NO 150
<211> LENGTH: 9
<212> TYPE: PRT
<213> ORGANISM: Artificial Sequence
<220> FEATURE:
<223> OTHER INFORMATION: Synthetic (CDR-L3 of Anti-Annexin A1 antibody)
<220> FEATURE:
<221> NAME/KEY: VARIANT
<222> LOCATION: (1)..(1)
<223> OTHER INFORMATION: Xaa is Gly(G) or Ala(A)
<220> FEATURE:
<221> NAME/KEY: VARIANT
<222> LOCATION: (2)..(2)
<223> OTHER INFORMATION: Xaa is Thr(T), Ser(S), or Ala(A)
<220> FEATURE:
<221> NAME/KEY: VARIANT
<222> LOCATION: (5)..(5)
<223> OTHER INFORMATION: Xaa is Asp(D), Tyr(Y), Ser(S), or Ala(A)
<220> FEATURE:
<221> NAME/KEY: VARIANT
<222> LOCATION: (8)..(8)
<223> OTHER INFORMATION: Xaa is Asn(N) or Ser(S)
<220> FEATURE:
<221> NAME/KEY: VARIANT
<222> LOCATION: (9)..(9)
<223> OTHER INFORMATION: Xaa is Gly(G) or Ala(A)

<400> SEQUENCE: 150

Xaa Xaa Trp Asp Xaa Ser Leu Xaa Xaa
1               5

<210> SEQ ID NO 151
<211> LENGTH: 30
<212> TYPE: PRT
<213> ORGANISM: Artificial Sequence
<220> FEATURE:
<223> OTHER INFORMATION: Synthetic (N-terminus of Annexin A1)

<400> SEQUENCE: 151

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly
            20                  25                  30

<210> SEQ ID NO 152
<211> LENGTH: 346
<212> TYPE: PRT
<213> ORGANISM: Artificial Sequence
<220> FEATURE:
<223> OTHER INFORMATION: Synthetic (full-length sequence of Annexin A1)

<400> SEQUENCE: 152

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80
```

```
                        -continued

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 153
<211> LENGTH: 19
<212> TYPE: DNA
<213> ORGANISM: Artificial Sequence
<220> FEATURE:
<223> OTHER INFORMATION: Synthetic (PC3X Foward primer)

<400> SEQUENCE: 153
gcacgacagg tttcccgac                                              19

<210> SEQ ID NO 154
<211> LENGTH: 20
<212> TYPE: DNA
<213> ORGANISM: Artificial Sequence
<220> FEATURE:
<223> OTHER INFORMATION: Synthetic (PC3X Reverse primer)

<400> SEQUENCE: 154
aaccatcgat agcagcaccg                                             20

<210> SEQ ID NO 155
<211> LENGTH: 22
<212> TYPE: DNA
```

<213> ORGANISM: Artificial Sequence
<220> FEATURE:
<223> OTHER INFORMATION: Synthetic (Sequencing primer)

<400> SEQUENCE: 155
aagacagcta tcgcgattgc ag                                                    22

POLYPEPTIDE BINDING TO ANNEXIN A1 AND USE THEREOF

CROSS-REFERENCE TO RELATED APPLICATIONS

This application claims the benefit of Korean Patent Application No. 10-2013-0108686 filed on Sep. 10, 2013 in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 58,754 bytes ASCII (Text) file named "718364_ST25.TXT" created Sep. 10, 2014.

BACKGROUND

1. Field

Provided is a polypeptide which specifically binds to and inhibits Annexin A1, methods utilizing the same for preventing, treating, or diagnosis disease, and related compositions and methods.

2. Description of the Related Art

Antibodies initiate their biological activities by binding to antigens. Generally, an antibody is specific to an antigen, with high affinity Antibodies are produced by B-lymphocytes. Blood contains a lot of different antibodies each of which is derived from a B-cell clone and has a characteristic structure and specificity with regard to its antigen.

Annexin has been used as a common name for a group of proteins including lipocortin, calpactin, endonexin, etc. since about 20 years ago. Annexin proteins bind phospholipids in a calcium-dependent manner. Each annexin is characterized by four (or sometimes eight) copies of about 70 amino acid repeat sequence containing a highly conserved 'GXGTDE' motif, also called endonexin-fold. All of the annexin proteins identified thus far are found to contain the conserved domains, and one of the criteria that a protein has to meet to be classified as an annexin is the existence of the domain.

Annexin proteins are found in a broad spectrum of organisms from mold fungi to mammals. Humans are reported to have annexin I, II, III, IV, V, VI, VII, VIII and XIII. Annexin proteins are speculated to play an important role in the formation of osseous tissues and to be involved in various biological activities including membrane trafficking, transmembrane channel activity, inhibition of phospholipase A2, coagulation inhibition, transduction of mitogen signals, and mediation of cell-matrix interaction, etc. Of the annexin proteins, Annexin A1, which belongs to the annexin A group, is known to be detected in cancer tissues as well.

Given the extensive research into the development of anticancer agents using proteins overexpressed in cancer cells, the significance of Annexin A1 as an anticancer target is growing, with a need for the development of an effective and potent Annexin A1-targeting drug.

SUMMARY

Provided herein is a polypeptide specifically binding to Annexin A1. In some embodiments, the polypeptide is an antagonist against Annexin A1.

Also provided is an anti-Annexin A1 antibody that specifically binds to Annexin A1, and an antigen-binding fragment thereof.

Further provided is a pharmaceutical composition useful for the prevention and/or treatment of a disease associated with the activation and/or overexpression of annex A1, including the anti-Annexin A1 antibody or the antigen-binding fragment thereof; and/or the Annexin A1 antagonist as an active ingredient.

Also provided is a method of preventing and/or treating a disease associated with the activation and/or overexpression of annex A1, including administering the anti-Annexin A1 antibody or the antigen-binding fragment thereof; and/or the Annexin A1 antagonist, to a subject in need thereof.

Another embodiment provides a composition for the detection of annex A1 or the diagnosis of a disease associated with the activation or overexpression of annex A1, the composition including the anti-Annexin A1 antibody or the antigen-binding fragment thereof; and/or the Annexin A1 antagonist.

Another embodiment provides a method of detecting annex A1 using the anti-Annexin A1 antibody or the antigen-binding fragment thereof; and/or the Annexin A1 antagonist.

Still another embodiment provides a method of diagnosing a disease associated with the activation or overexpression of annex A1, using the anti-Annexin A1 antibody or the antigen-binding fragment thereof; and/or the Annexin A1 antagonist.

BRIEF DESCRIPTION OF THE DRAWINGS

FIG. 5 is an alignment (CLUSTAL W (1.8) multiple sequence alignment) of 10 representative scFv amino acid sequences that bind to an Annexin A1 N-terminus or a full-length Annexin A1 protein.

FIG. 10 is a graph showing binding intensities of the Annexin A1-binding scFv selected depending on their concentrations in SNU1 and MDA-MB-453, as measured by FACS.

DETAILED DESCRIPTION

Figure 1:
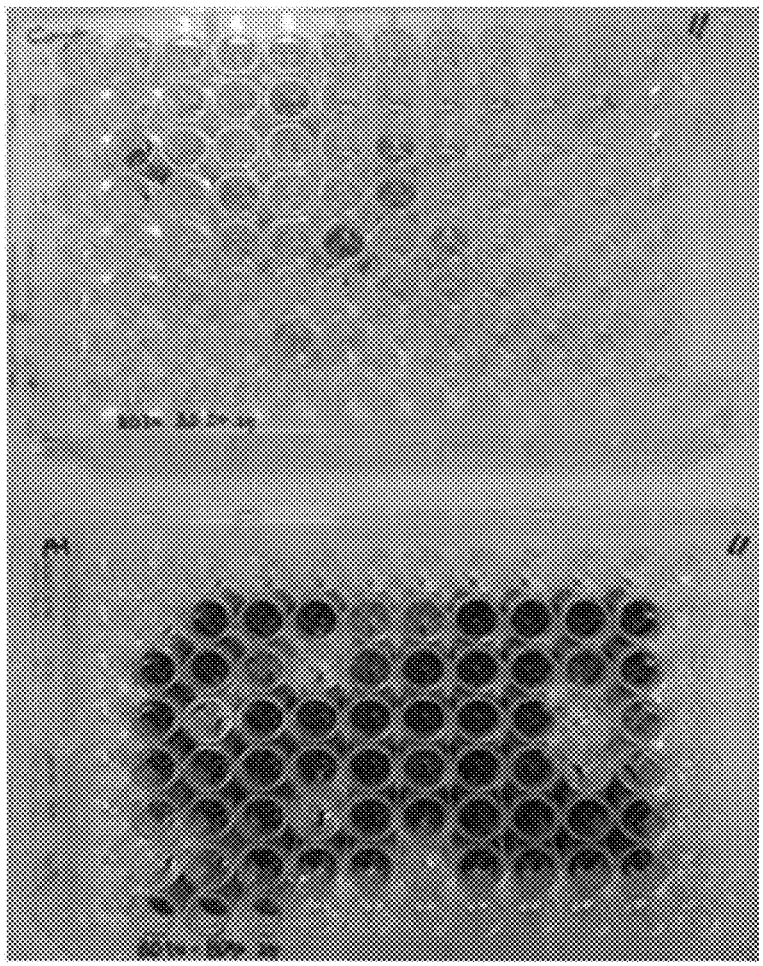
FIG. 1 is an image showing ELISA analysis results for the scFv pool binding to an N-terminal region obtained after 3 rounds of the biopanning process.

The present disclosure pertains to a novel polypeptide that binds to Annexin A1, and the use thereof. More particularly, the present disclosure concerns a novel polypeptide that binds to an Annexin A1 protein or a fragment of Annexin A1, and the use thereof.

Annexin A1 participates in cell-to-cell signaling, and performs its functions in a calcium-dependent manner. In addition, Annexin A1 is considered to be a factor that has an influence on the growth and metastasis of cancer cells, and is reported to be overexpressed in various cancer cells. Using a phage library screening technique, the present inventors have exploited a novel polypeptide capable of binding to Annexin A1, with the aim of applying it to the diagnosis and treatment of Annexin A1-related diseases.

One aspect of the present disclosure is a polypeptide having a novel amino acid sequence. This polypeptide binds specifically to Annexin A1, and, in one embodiment, to full-length Annexin A1 or an extracellular portion thereof (for example, an N-terminal region ranging in length from 20 to 40 amino acid residues, or from 25 to 35 amino acid residues) to inhibit the function of Annexin A1.

In an embodiment, the polypeptide may be selected from the group consisting of:

a polypeptide including at least one selected from the group consisting of amino acid sequences set forth in SEQ ID NO: 2 and SEQ ID NO: 147 (General Formula 1);

a polypeptide including at least one selected from the group consisting of amino acid sequences set forth in SEQ ID NO: 12 to SEQ ID NO: 42;

a polypeptide including at least one selected from the group consisting of amino acid sequences set forth in SEQ ID NO: 48, SEQ ID NO: 61, SEQ ID NO: 63, SEQ ID NO: 67, SEQ ID NO: 70, SEQ ID NO: 73, and SEQ ID NO: 148 (General Formula 2);

a polypeptide including the amino acid sequence of SEQ ID NO: 149 (General Formula 3);

a polypeptide including at least one selected from the group consisting of amino acid sequences set forth in SEQ ID NO: 95 to SEQ ID NO: 112;

a polypeptide including at least one selected from the group consisting of amino acid sequences set forth in SEQ ID NO: 135 and SEQ ID NO: 150 (General Formula 4); and a combination thereof.

General Formula 1
(SEQ ID NO: 147)
X1-Y-X2-M-S wherein X1 is Asn(N), Gly(G), Asp(D), or Ser(S),
X2 is Ala(A), Ser(S), or Tyr(Y);

General Formula 2
(SEQ ID NO: 148)
X3-X4-X5-X6-X7-F-D-Y wherein X3 is Arg(R) or Lys(K),
X4 is Arg(R), Gly(G), Ala(A), Met(M), Lys(K), Ser(S), or Asn(N),
X5 is Ala(A), Ser(S), Leu(L), Ile(I), Thr(T), Val(V), Gly(G), Asn(N), Pro(P), or Lys(K),
X6 is Ile(I), Pro(P), Gly(G), His(H), Thr(T), Ser(S), Ala(A), Asn(N), Trp(W), Lys(K), or Gln(Q),
X7 is Arg(R), Leu(L), Ile(I), Pro(P), Gly(G), Ser(S), Thr(T), or Val(V), General Formula 3
(SEQ ID NO: 149)
X8-G-X9-S-X10-N-I-G-X11-N-X12-V-X13 wherein X8 is Ser(S) or Thr(T),
X9 is Ser(S) or Thr(T),
X10 is Ser(S) or Phe(F),
X11 is Ser(S), Asn(N), or Ile(I),
X12 is Asp(D), Ser(S), Asn(N), Ala(A), Thr(T), or Tyr(Y),
X13 is Thr(T), Asn(N), or Ser(S), General Formula 4
(SEQ ID NO: 150)
X14-X15-W-D-X16-S-L-X17-X18 wherein X14 is Gly(G) or Ala(A),
X15 is Thr(T), Ser(S), or Ala(A),
X16 is Asp(D), Tyr(Y), Ser(S), or Ala(A),
X17 is Asn(N) or Ser(S),
X18 is Gly(G) or Ala(A).

In an embodiment, the polypeptide is selected from the group consisting of:

a polypeptide including at least one amino acid sequence selected from the group consisting of amino acid sequences set forth in SEQ ID NO: 1 to SEQ ID NO: 11;

a polypeptide including at least one amino acid sequence selected from the group consisting of amino acid sequences set forth in SEQ ID NO: 12 to SEQ ID NO: 42;

a polypeptide including at least one amino acid sequence selected from the group consisting of amino acid sequences set forth in SEQ ID NO: 43 to SEQ ID NO: 74;

a polypeptide including at least one amino acid sequence selected from the group consisting of amino acid sequences set forth in SEQ ID NO: 75 to SEQ ID NO: 94;

a polypeptide including at least one amino acid sequence selected from the group consisting of amino acid sequences set forth in SEQ ID NO: 95 to SEQ ID NO: 112;

a polypeptide including at least one amino acid sequence selected from the group consisting of amino acid sequences set forth in SEQ ID NO: 113 to SEQ ID NO: 136; and a combination thereof.

In one embodiment, the polypeptide is selected from the group consisting of:

a polypeptide including at least one amino acid sequence selected from the group consisting of amino acid sequences set forth in SEQ ID NO: 1 to SEQ ID NO: 6;

a polypeptide including at least one amino acid sequence selected from the group consisting of amino acid sequences set forth in SEQ ID NO: 12 to SEQ ID NO: 26;

a polypeptide including at least one amino acid sequence selected from the group consisting of amino acid sequences set forth in SEQ ID NO: 43 to SEQ ID NO: 57;

a polypeptide including at least one amino acid sequence selected from the group consisting of amino acid sequences set forth in SEQ ID NO: 75 to SEQ ID NO: 85;

a polypeptide including at least one amino acid sequence selected from the group consisting of amino acid sequences set forth in SEQ ID NO: 95 to SEQ ID NO: 100;

a polypeptide including at least one amino acid sequence selected from the group consisting of amino acid sequences set forth in SEQ ID NO: 113 to SEQ ID NO: 122; and a combination thereof. In this case, the polypeptide may have the function of binding specifically to an N terminus (for example, an N terminal region including 20 to 30 contiguous amino acid residues, or 25 to 35 contiguous amino acid residues; e.g., SEQ ID NO: 151) of Annexin A1 or a region including 2 to 30 contiguous amino acid residues, 5 to 25 contiguous amino acid residues, or 10 to 20 contiguous amino acid residues within the N-terminal region.

In another embodiment, the polypeptide is selected from the group consisting of:

a polypeptide including at least one selected from the group consisting of amino acid sequences set forth in SEQ ID NO: 7 to SEQ ID NO: 11;

a polypeptide including at least one selected from the group consisting of amino acid sequences set forth in SEQ ID NO: 27 to SEQ ID NO: 42;

a polypeptide including at least one selected from the group consisting of amino acid sequences set forth in SEQ ID NO: 58 to SEQ ID NO: 74;

a polypeptide including at least one selected from the group consisting of amino acid sequences set forth in SEQ ID NO: 86 to SEQ ID NO: 94;

a polypeptide including at least one selected from the group consisting of amino acid sequences set forth in SEQ ID NO: 101 to SEQ ID NO: 112;

a polypeptide including at least one selected from the group consisting of amino acid sequences set forth in SEQ ID NO: 123 to SEQ ID NO: 136; and a combination thereof.

The polypeptide may have the function of binding specifically to full-length Annexin A1 (e.g., Accession No. NP_000691.1, SEQ ID NO: 152), or a region including 2 to 30 contiguous amino acid residues, 5 to 25 contiguous amino acid residues, or 10 to 20 contiguous amino acid residues within the full-length protein, wherein the contiguous amino acid residues refers that the amino acids are located contiguously on the primary, secondary or tertiary structure of the full-length protein.

The polypeptide including an amino acid sequence selected from among SEQ ID NOS: 1 to 150 (or some combination thereof) functions as an Annexin A1 inhibitor by specifically binding annexin 1 (full-length or extracellular region (e.g., N-terminus)), and thus may be used as a complementarity-determining region of an anti-Annexin A1 antibody. The functions of the polypeptides in anti-annexin antibodies are summarized in Tables 1 and 2, below.

TABLE 1

| Heavy chain complementarity determining region | | |
|---|---|---|
| CDR-H1 | CDR-H2 | CDR-H3 |
| NYAMS (SEQ ID NO: 1) | AISPGDSNT (SEQ ID NO: 12) | RMTKRFDY (SEQ ID NO: 43) |
| NYAMS (SEQ ID NO: 1) | GIYPNSGSNT (SEQ ID NO: 13) | RRPTLFDY (SEQ ID NO: 44) |
| DYSMG (SEQ ID NO: 2) | GIYPSGGNT (SEQ ID NO: 14) | RKPTIFDY (SEQ ID NO: 45) |
| NYAMS (SEQ ID NO: 1) | AIYPGGGSI (SEQ ID NO: 15) | RRLQIFDY (SEQ ID NO: 46) |
| GYSMS (SEQ ID NO: 3) | GIYSGDSSK (SEQ ID NO: 16) | RSLSIFDY (SEQ ID NO: 47) |
| NYAMS (SEQ ID NO: 1) | GISSDDGSKY (SEQ ID NO: 17) | ARTLTIFDY (SEQ ID NO: 48) |
| DYAMS (SEQ ID NO: 4) | GIYPSSSSK (SEQ ID NO: 18) | KRLALFDY (SEQ ID NO: 49) |
| NYAMS (SEQ ID NO: 1) | GISSDNSSKY (SEQ ID NO: 19) | RRISLFDY (SEQ ID NO: 50) |
| GYSMS (SEQ ID NO: 3) | GIYYGDGST (SEQ ID NO: 20) | RRATLFDY (SEQ ID NO: 51) |
| NYAMS (SEQ ID NO: 1) | AIYPGNGSK (SEQ ID NO: 21) | KGLSLFDY (SEQ ID NO: 52) |
| GYAMS (SEQ ID NO: 5) | GIYPGGGST (SEQ ID NO: 22) | RRLTIFDY (SEQ ID NO: 53) |
| DYSMG (SEQ ID NO: 2) | GIYPSGGNT (SEQ ID NO: 14) | KRPSRFDY (SEQ ID NO: 54) |
| GYSMS (SEQ ID NO: 3) | GIYPGGSST (SEQ ID NO: 23) | KRPTLFDY (SEQ ID NO: 55) |
| DYAMS (SEQ ID NO: 4) | AIYPDGGST (SEQ ID NO: 24) | KRITLFDY (SEQ ID NO: 56) |
| SYAMS (SEQ ID NO: 6) | GIYPSDGNI (SEQ ID NO: 25) | KNKAPFDY (SEQ ID NO: 57) |
| DYAMS (SEQ ID NO: 4) | GIYPSSSSK (SEQ ID NO: 18) | KRLALFDY (SEQ ID NO: 49) |

TABLE 1-continued

Heavy chain complementarity determining region

| CDR-H1 | CDR-H2 | CDR-H3 |
|---|---|---|
| NYAMS (SEQ ID NO: 1) | AIYPSNGSK (SEQ ID NO: 26) | KGLSLFDY (SEQ ID NO: 52) |
| NYSMS (SEQ ID NO: 7) | GISSDGGNK (SEQ ID NO: 27) | RRAIPFDY (SEQ ID NO: 58) |
| GYYMS (SEQ ID NO: 8) | SISPSGSSI (SEQ ID NO: 28) | KGSPGFDY (SEQ ID NO: 59) |
| DYAMS (SEQ ID NO: 4) | GISYGGGNT (SEQ ID NO: 29) | KRLGSFDY (SEQ ID NO: 60) |
| NYAMS (SEQ ID NO: 1) | SISSNSGNK (SEQ ID NO: 30) | KATLGMDHIHAYSAYGMDV (SEQ ID NO: 61) |
| SYSMS (SEQ ID NO: 9) | GISPGSGSI (SEQ ID NO: 31) | RRIHPFDY (SEQ ID NO: 62) |
| DYSMS (SEQ ID NO: 10) | VISPDSSNT (SEQ ID NO: 32) | KVTGTCGPRSCYYYDAMDV (SEQ ID NO: 63) |
| DYSMS (SEQ ID NO: 10) | SISPDGGNK (SEQ ID NO: 33) | KRTTLFDY (SEQ ID NO: 64) |
| NYSMS (SEQ ID NO: 7) | GISPDGGSI (SEQ ID NO: 34) | RRSSLFDY (SEQ ID NO: 65) |
| GYYMS (SEQ ID NO: 8) | SISPSGSSI (SEQ ID NO: 28) | KGSPGFDY (SEQ ID NO: 59) |
| NYSMS (SEQ ID NO: 7) | GISPDDGSI (SEQ ID NO: 35) | RRVGLFDY (SEQ ID NO: 66) |
| SYYMS (SEQ ID NO: 11) | LISPGSGSI (SEQ ID NO: 36) | RSISGRQYANPSYDDAMDV (SEQ ID NO: 67) |
| SYSMS (SEQ ID NO: 9) | GISPNGGSI (SEQ ID NO: 37) | KRAALFDY (SEQ ID NO: 68) |
| NYSMS (SEQ ID NO: 7) | AISSSGGST (SEQ ID NO: 38) | RRGNLFDY (SEQ ID NO: 69) |
| SYYMS (SEQ ID NO: 11) | LISPGSGSI (SEQ ID NO: 36) | KGGPARRASTFDY (SEQ ID NO: 70) |
| NYSMS (SEQ ID NO: 7) | SISPSSGSI (SEQ ID NO: 39) | KRNWTFDY (SEQ ID NO: 71) |
| NYSMS (SEQ ID NO: 7) | LISPDSSSI (SEQ ID NO: 40) | KRATVFDY (SEQ ID NO: 72) |
| NYAMS (SEQ ID NO: 1) | SISYGNSNK (SEQ ID NO: 41) | RAPGPFNY (SEQ ID NO: 73) |
| NYSMS (SEQ ID NO: 7) | AISSDGGST (SEQ ID NO: 42) | RRGALFDY (SEQ ID NO: 74) |

TABLE 2

Light chain complementarity determining region

| CDR-L1 | CDR-L2 | CDR-L3 |
|---|---|---|
| SGSSSNIGSNDVT (SEQ ID NO: 75) | DNSK (SEQ ID NO: 95) | GTWDDSLNG (SEQ ID NO: 113) |
| TGSSSNIGSNSVN (SEQ ID NO: 76) | SDSH (SEQ ID NO: 96) | ATWDDSLNG (SEQ ID NO: 114) |
| SGSSSNIGNNDVN (SEQ ID NO: 77) | SNSH (SEQ ID NO: 97) | GTWDDSLNG (SEQ ID NO: 113) |
| TGSSSNIGSNNVT (SEQ ID NO: 78) | SDSH (SEQ ID NO: 96) | GSWDYSLSA (SEQ ID NO: 115) |
| SGSSSNIGSNAVT (SEQ ID NO: 79) | SNSQ (SEQ ID NO: 98) | GTWDYSLSG (SEQ ID NO: 116) |

TABLE 2-continued

Light chain complementarity determining region

| CDR-L1 | CDR-L2 | CDR-L3 |
|---|---|---|
| SGSSSNIGSNNVT(SEQ ID NO: 89) | SDSH(SEQ ID NO: 96) | GTWDYSLSG(SEQ ID NO: 116) |
| SGSSSNIGNNAVN(SEQ ID NO: 81) | SNSH(SEQ ID NO: 97) | GAWDYSLSG(SEQ ID NO: 117) |
| TGSSSNIGSNNVT(SEQ ID NO: 78) | SDSH(SEQ ID NO: 96) | GSWDYSLSA(SEQ ID NO: 115) |
| TGSSSNIGSNSVS(SEQ ID NO: 82) | SDNH(SEQ ID NO: 99) | GTWDYSLSG(SEQ ID NO: 116) |
| TGSSSNIGSNNVT(SEQ ID NO: 78) | SDSH(SEQ ID NO: 96) | GAWDYSLNA(SEQ ID NO: 118) |
| SGSSSNIGNNDVT(SEQ ID NO: 83) | SDSH(SEQ ID NO: 96) | GTWDDSLSG(SEQ ID NO: 119) |
| TGSSSNIGNNDVN(SEQ ID NO: 84) | SNSH(SEQ ID NO: 97) | GTWDDSLNG(SEQ ID NO: 113) |
| TGSSSNIGSNNVT(SEQ ID NO: 78) | ADSN(SEQ ID NO: 100) | GTWDDSLSA(SEQ ID NO: 120) |
| TGSSSNIGSNNVT(SEQ ID NO: 78) | SDSH(SEQ ID NO: 96) | GTWDYSLSG(SEQ ID NO: 116) |
| TGSSSNIGNNTVS(SEQ ID NO: 85) | SDSH(SEQ ID NO: 96) | ATWDDSLNA(SEQ ID NO: 121) |
| SGSSSNIGNNAVN(SEQ ID NO: 81) | SNSH(SEQ ID NO: 97) | GAWDYSLSG(SEQ ID NO: 117) |
| TGSSSNIGSNNVT(SEQ ID NO: 78) | SDSH(SEQ ID NO: 96) | GAWDYSLNG(SEQ ID NO: 122) |
| TGSSSNIGSNAVS(SEQ ID NO: 86) | YNSQ(SEQ ID NO: 101) | GAWDDSLNA(SEQ ID NO: 123) |
| SGSSFNIGSNDVS(SEQ ID NO: 87) | SDSH(SEQ ID NO: 96) | GSWDYSLSA(SEQ ID NO: 115) |
| TGTSSNIGSNYVS(SEQ ID NO: 88) | AGNH(SEQ ID NO: 102) | GSWDSSLSA(SEQ ID NO: 124) |
| TGSSSNIGSNSVS(SEQ ID NO: 82) | ANSN(SEQ ID NO: 103) | AAWDDSLNA(SEQ ID NO: 125) |
| TGSSSNIGNNDVS(SEQ ID NO: 89) | SDNQ(SEQ ID NO: 104) | GAWDSSLNA(SEQ ID NO: 126) |
| SGSSSNIGSNAVS(SEQ ID NO: 90) | YNSH(SEQ ID NO: 105) | ATWDSSLNG(SEQ ID NO: 127) |
| TGSSSNIGSNDVS(SEQ ID NO: 91) | DNSQ(SEQ ID NO: 106) | AAWDASLSA(SEQ ID NO: 128) |
| TGSSSNIGNNSVT(SEQ ID NO: 92) | DSQR(SEQ ID NO: 107) | GSWDASLSA(SEQ ID NO: 129) |
| SGSSFNIGSNDVS(SEQ ID NO: 87) | SDSH(SEQ ID NO: 96) | GSWDYSLSA(SEQ ID NO: 115) |
| TGSSSNIGNNDVS(SEQ ID NO: 89) | YDNQ(SEQ ID NO: 108) | GAWDASLSA(SEQ ID NO: 130) |
| SGSSSNIGSNNVT(SEQ ID NO: 80) | ANSN(SEQ ID NO: 103) | GAWDDSLSG(SEQ ID NO: 131) |
| SGSSSNIGSNDVT(SEQ ID NO: 75) | YDSN(SEQ ID NO: 109) | GAWDYSLNG(SEQ ID NO: 122) |
| TGSSSNIGSNDVS(SEQ ID NO: 91) | DDSN(SEQ ID NO: 110) | GSWDASLNG(SEQ ID NO: 132) |
| SGSSFNIGSNDVS(SEQ ID NO: 87) | DNSK(SEQ ID NO: 111) | GSWDDSLSG(SEQ ID NO: 133) |
| TGSSSNIGNNDVS(SEQ ID NO: 89) | SDNQ(SEQ ID NO: 104) | GAWDSSLNA(SEQ ID NO: 126) |
| SGSSSNIGSNDVS(SEQ ID NO: 93) | YDSN(SEQ ID NO: 109) | GTWDSSLSG(SEQ ID NO: 134) |
| TGSSSNIGINDVS(SEQ ID NO: 94) | ADNN(SEQ ID NO: 112) | AACDDNLND(SEQ ID NO: 135) |
| TGSSSNIGNNDVS(SEQ ID NO: 89) | YNSQ(SEQ ID NO: 101) | GSWDDSLSA(SEQ ID NO: 136) |

In one embodiment, the polypeptide may contain an amino acid sequence selected from the group consisting of SEQ ID NO: 137 to SEQ ID NO: 146.

For example, the polypeptide may be one including an amino acid sequence selected from the group consisting of SEQ ID NO: 137 to SEQ ID NO: 140. In this case, the polypeptide may specifically bind to an N-terminal region (having a length of 20 to 40 amino acid residues, or 25 to 35 amino acid residues; e.g., SEQ ID NO: 151) of Annexin A1, or a region including 2 to 30 contiguous amino acid residues, 5 to 25 contiguous amino acid residues, or 10 to 20 contiguous amino acid residues within the N-terminal region. In an environment where Annexin A1 is partially exposed to the outside of the cell (for example, in the presence of calcium), the N-terminal region of Annexin A1 may be not a cell-bound portion of Annexin A1, but an extracellular portion of Annexin A1. The polypeptide may specifically bind to the exposed N-terminal region of Annexin A1.

Alternatively, the polypeptide may include an amino acid sequence selected from the group consisting of SEQ ID NO: 141 to SEQ ID NO: 146. In this context, the polypeptide may specifically bind to full-length Annexin A1 (e.g., Accession No. NP_000691.1), or a region including 2 to 30 contiguous amino acid residues, 5 to 25 contiguous amino acid residues, or 10 to 20 contiguous amino acid residues within the full-length protein wherein the contiguous amino acid residues refers that the amino acids are located contiguously on the primary, secondary or tertiary structure of the full-length protein. In an environment where Annexin A1 is exposed to the outside of the cell (for example, in the presence of calcium), the full-length Annexin A1 or its region may be not a cell-bound portion of Annexin A1, but an extracellular portion of Annexin A1.

The polypeptide may be non-naturally occurring or synthetic.

As mentioned above, the polypeptide specifically binds to Annexin A1 (full length or partial), showing inhibitory activity against the Annexin A1. Therefore, the polypeptide may serve as a precursor or as one or more components of an Annexin A1 antagonist, for example, an anti-Annexin A1 antibody, an antigen-binding fragment of the antibody, or an anti-Annexin A1 antibody analogue (a structure similar in framework and function to the antibody; for example, a peptibody, a nanobody, etc.).

Accordingly, an embodiment provides an Annexin A1 antagonist including at least one of the polypeptides. The antagonist, which is inhibitory of Annexin A1, may be selected from the group consisting of an anti-Annexin A1 antibody, an antigen-binding fragment of the antibody, an anti-Annexin A1 antibody analogue (for example, a peptibody, a nanobody, a bispecific antibody, a multispecific antibody, etc.), and a combination thereof.

As used herein, the term "antagonist" is construed to encompass all molecules that partially or completely block, suppress or neutralize one or more biological activities of a target (e.g., Annexin A1). For example, an "antagonist" antibody means an antibody which suppresses or reduces the biological activity of the antigen (e.g., Annexin A1) bound thereby. An antagonist binds a material which interacts with a target, to decrease the activity of the material, for example, leading to the incapacitation or death of cells which are activated by the material. Alternatively, an antagonist may discontinue interaction between the target and the material, or may substantially reduce the interaction by competing with the target for the material or by altering the tertiary structure of the material or down-regulating the material.

The term "peptibody", as used herein, means a fusion protein (peptide+antibody) mimicking an antibody in terms of framework and function in which a peptide is fused to a partial or entire constant region, e.g., Fc, of an antibody and serves as an antigen-binging fragment (heavy chain and/or light chain CDR or variable region).

The term "nanobody," also called single-domain antibody, as used herein, refers to an antibody fragment which possesses a monomeric single variable domain of an antibody and shows selectivity for certain antigens, like an intact antibody. Its molecular weights generally ranges from about 12 kDa to about 15 kDa, which is much smaller than that of an intact antibody (about 150 kDa to about 160 kDa, inclusive of two heavy chains and two light chains) and, in some cases, even than that of an Fab or scFv fragment.

The term "bispecific antibody," or "multispecific antibody," refers to an antibody which recognizes and/or binds two (bispecific) or more (multispecific) different antigens, or two or more sites of the same antigen and, as used herein, is intended to encompass a bispecific antibody or a multispecific antibody in which the polypeptide functions as one antigen-binding site.

In accordance with a further aspect, the present disclosure provides an anti-Annexin A1 antibody or an antigen-binding fragment thereof, including a polypeptide. The anti-Annexin A1 antibody or an antigen-binding fragment thereof specifically recognizes or binds Annexin A1. The antigen-binding fragment may be selected from the group consisting of scFv, $(scFv)_2$, scFv-Fc, Fab, Fab' and $F(ab')_2$.

Particularly, the anti-Annexin A1 antibody or an antigen-binding fragment thereof may comprise or consist essentially of:

at least one heavy chain complementarity determining region (CDR) selected from the group consisting of CDR-H1 comprising an amino acid sequence selected from the group consisting of SEQ ID NO: 2 and SEQ ID NO: 147 (General Formula 1), CDR-H2 comprising an amino acid sequence selected from the group consisting of SEQ ID NO: 12 to SEQ ID NO: 42, and CDR-H3 comprising an amino acid sequence selected from the group consisting of SEQ ID NO: 48, SEQ ID NO: 61, SEQ ID NO: 63, SEQ ID NO: 67, SEQ ID NO: 70, SEQ ID NO: 73, and SEQ ID NO: 148 (General Formula 2), or a heavy chain variable region including the at least one heavy chain complementarity determining region;

at least one light chain complementarity determining region (CDR) selected from the group consisting of CDR-L1 comprising an amino acid sequence of SEQ ID NO: 149 (General Formula 3), CDR-L2 comprising an amino acid sequence selected from the group consisting of SEQ ID NO: 95 to SEQ ID NO: 112, and CDR-L3 comprising an amino acid sequence selected from the group consisting of SEQ ID NO: 135 to SEQ ID NO: 150 (General Formula 4), or a heavy chain variable region including the at least one light chain complementarity determining region;

a combination of the at least one heavy chain complementarity determining region and the at least one light chain complementarity determining region; or a combination of the heavy chain variable region and the light chain variable region.

The amino acid sequences of General Formulas 1 to 4 are as defined above.

More particularly, the anti-Annexin A1 antibody or an antigen-binding fragment thereof may comprise or consist essentially of:

at least one heavy chain complementarity determining region selected from the group consisting of CDR-H1 comprising an amino acid sequence selected from the group consisting of SEQ ID NO: 1 to SEQ ID NO: 11, CDR-H2 comprising an amino acid sequence selected from the group consisting of SEQ ID NO: 12 to SEQ ID NO: 42, and CDR-H3 comprising an amino acid sequence selected from the group consisting of SEQ ID NO: 43 to SEQ ID NO: 74, or a heavy chain variable region including the at least one heavy chain complementarity determining region;

at least one light chain complementarity determining region (CDR) selected from the group consisting of CDR-L1 comprising an amino acid sequence of SEQ ID NO: 75 to SEQ ID NO: 94, CDR-L2 comprising an amino acid sequence selected from the group consisting of SEQ ID NO: 95 to SEQ ID NO: 112, and CDR-L3 comprising an amino acid sequence selected from the group consisting of SEQ ID NO: 113 to SEQ ID NO: 136, or a light chain variable region including the light chain complementarity determining region;

a combination of at least one heavy chain complementarity determining region and the at least one light chain complementarity determining region; or a combination of the heavy chain variable region and the light chain variable region.

In one embodiment, the anti-Annexin A1 antibody or an antigen-binding fragment thereof may comprise or consist essentially of:

at least one heavy chain complementarity determining region selected from the group consisting of CDR-H1 comprising an amino acid sequence selected from the group consisting of SEQ ID NO: 1 to SEQ ID NO: 6, CDR-H2 comprising an amino acid sequence selected from the group consisting of SEQ ID NO: 12 to SEQ ID NO: 26, and CDR-H3 comprising an amino acid sequence selected from the group consisting of SEQ ID NO: 43 to SEQ ID NO: 57, or a heavy chain variable region including the at least one heavy chain complementarity determining region;

at least one light chain complementarity determining region (CDR) selected from the group consisting of CDR-L1 comprising an amino acid sequence of SEQ ID NO: 75 to SEQ ID NO: 85, CDR-L2 comprising an amino acid sequence selected from the group consisting of SEQ ID NO: 95 to SEQ ID NO: 100, and CDR-L3 comprising an amino acid sequence selected from the group consisting of SEQ ID NO: 113 to SEQ ID NO: 122, or a light chain variable region including the light chain complementarity determining region;

a combination of at least one heavy chain complementarity determining region and at least one light chain complementarity determining region; or a combination of the heavy chain variable region and the light chain variable region. In this case, the anti-Annexin A1 antibody or an antigen-binding fragment thereof may specifically recognize and/or bind to an N-terminal region (for example, an N terminal region including 20 to 30 contiguous amino acid residues, or 25 to 35 contiguous amino acid residues; e.g., SEQ ID NO: 151) of Annexin A1, or a region including 2 to 30 contiguous amino acid residues, 5 to 25 contiguous amino acid residues, or 10 to 20 contiguous amino acid residues within the N-terminal region.

In another embodiment, the anti-Annexin A1 antibody or an antigen-binding fragment thereof may comprise or consist essentially of:

at least one heavy chain complementarity determining region selected from the group consisting of CDR-H1 comprising an amino acid sequence selected from the group consisting of SEQ ID NO: 7 to SEQ ID NO: 11, CDR-H2 comprising an amino acid sequence selected from the group consisting of SEQ ID NO: 27 to SEQ ID NO: 42, and CDR-H3 comprising an amino acid sequence selected from the group consisting of SEQ ID NO: 58 to SEQ ID NO: 74, or a heavy chain variable region including the at least one heavy chain complementarity determining region;

at least one light chain complementarity determining region (CDR) selected from the group consisting of CDR-L1 comprising an amino acid sequence of SEQ ID NO: 86 to SEQ ID NO: 94, CDR-L2 comprising an amino acid sequence selected from the group consisting of SEQ ID NO: 101 to SEQ ID NO: 112, and CDR-L3 comprising an amino acid sequence selected from the group consisting of SEQ ID NO: 123 to SEQ ID NO: 136, or a light chain variable region including the light chain complementarity determining region;

a combination of the at least one heavy chain complementarity determining region and at least one light chain complementarity determining region; or a combination of the heavy chain variable region and the light chain variable region.

In this case, the anti-Annexin A1 antibody or an antigen-binding fragment thereof may specifically recognize and/or bind to a full-length Annexin A1 protein (e.g., Accession No. NP_000691.1), or a region including 2 to 30 contiguous amino acid residues, 5 to 25 contiguous amino acid residues, or 10 to 20 contiguous amino acid residues within the full-length protein wherein the contiguous amino acid residues refers that the amino acids are located contiguously on the primary, secondary or tertiary structure of the full-length protein.

In one embodiment, the anti-Annexin A1 antibody or an antigen-binding fragment thereof may be an antibody or scFv including an amino acid sequence selected from the group consisting of SEQ ID NO: 137 to SEQ ID NO: 146. For example, the anti-Annexin A1 antibody or an antigen-binding fragment thereof may be an antibody or scFv including an amino acid sequence selected from the group consisting of SEQ ID NO: 137 to SEQ ID NO: 140. In this case, the anti-Annexin A1 antibody or an antigen-binding fragment thereof may specifically recognize and/or bind to an N-terminal region (having a length of 20 to 40 amino acid residues, or 25 to 35 amino acid residues; e.g., SEQ ID NO: 151) of Annexin A1, or a region including 2 to 30 contiguous amino acid residues, 5 to 25 contiguous amino acid residues, or 10 to 20 contiguous amino acid residues within the N-terminal region. In an alternative embodiment, the anti-Annexin A1 antibody or an antigen-binding fragment thereof may be an antibody or scFv including an amino acid sequence selected from the group consisting of SEQ ID NO: 141 to SEQ ID NO: 146. In this regard, the anti-Annexin A1 antibody or an antigen-binding fragment thereof may specifically recognize and/or bind to a full-length Annexin A1 protein (e.g., Accession No. NP_000691.1), or a region including 2 to 30 contiguous amino acid residues, 5 to 25 contiguous amino acid residues, or 10 to 20 contiguous amino acid residues within the full-length protein wherein the contiguous amino acid residues refers that the amino acids are located contiguously on the primary, secondary or tertiary structure of the full-length protein.

Examples of the antibody useful in the present disclosure include, but are not limited to, animal antibodies, chimeric antibodies, humanized antibodies, and human antibodies. Also, an isolated antigen-binding fragment of an antibody may fall into the scope of the antibody of the present disclosure. The term "complementarity-determining region" (CDR) refers to a variable region of an antigen which is critical to specificity for an antigen. The antigen-binding fragment described above may be an antigen fragment including at least one complementarity-determining region, such as one selected from among scFv, (scFv)$_2$, scFv-Fc, Fab, Fab' and F(ab')$_2$.

The rest parts of the anti-Annexin A1 antibody or an antigen-binding fragment thereof; that is, the part other than the heavy chain CDR, the light chain CDR, the heavy chain variable region, and/or the light chain variable region, as defined supra, for example, a heavy chain constant region, or the light chain constant region, may be derived from any subtype of immunoglobulins (e.g., IgA, IgD, IgE, IgG (IgG1, IgG2, IgG3, IgG4), IgM, etc.).

Annexin A1 (Annexin I) belongs to the annexin family of $Ca^{2+}$-dependent phospholipid-binding proteins. In the present disclosure, the Annexin A1 may originate from mammals including primates, such as humans and monkeys, and rodents such as rats and mice. By way of example, it may be human Annexin A1 (e.g., NCBI Accession No. NP_000691.1, etc.), rhesus Annexin A1 (e.g., NCBI Accession No. AFH29166.1, etc.), mouse Annexin A1 (NCBI Accession No. NP_034860.2, etc.), or rat Annexin A1 (e.g., NCBI Accession No. 001164623.1, etc.), which originate, as implied by their names, from humans, monkeys, mice, and rats, respectively.

When a medical treatment on humans is conducted therewith, animal-derived antibodies produced by immunizing non-immune animals with a desired antigen generally invoke immunogenicity. In the interests of suppressing such immune rejection, chimeric antibodies have been developed. Chimeric antibodies are prepared by replacing constant regions of animal-derived antibodies causing an anti-isotype response with those of human antibodies using a genetic engineering technique. Although significantly improved in anti-isotype response when compared to their original animal-derived antibodies, chimeric antibodies still retain the potential risk of side effects of anti-idiotype responses because of the animal-derived amino acids incorporated into the variable region thereof. Humanized antibodies were developed to reduce such side effects. Humanized antibodies are produced by grafting complementarity determining regions (CDRs), critical to antigen binding, of variable regions of chimeric antibodies to a human antibody framework.

One important aspect of the CDR grafting process in producing humanized antibodies is to choose a human antibody optimized for accepting CDRs of animal-derived antibodies. To this end, advantage is taken of antibody databases, crystal structure analysis, and molecular modeling techniques. However, even when CDRs of animal-derived antibodies are grafted to an optimized human antibody framework, there may be amino acids that are positioned in the framework of the animal-derived antibody that affect the antigen binding, which leads, in many cases, to a reduction in the antigen binding force. Hence, the production of humanized antibodies may require additional antibody engineering technology for recovering the antigen binding force.

According to one embodiment, the antibody may be a mouse-derived antibody, a mouse-human chimeric antibody, a humanized antibody, or a human antibody. The antibody may be monoclonal. The antibodies or antigen-binding fragments thereof may be isolated from a living body or non-naturally occurring. The antibodies or antigen-binding fragments thereof may be recombinant or synthetic.

An intact antibody consists of two full-length light chains and two full-length heavy chains, where each light chain is linked to the heavy chain by disulfide bonds. A constant region is present in each of the heavy and the light chains. The heavy chain constant region is of a gamma (γ), mu (μ), alpha (α), delta (δ), or epsilon (ε) type, which can be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" is intended to encompass a full-length heavy chain composed of a variable region $V_H$ including an amino acid sequence sufficient to confer specificity for an antigen on the antibody, three constant region domains ($C_{H1}$, $C_{H2}$, and $C_{H3}$), a hinge, and a fragment of the full-length heavy chain. The term "light chain" refers to a full-length light chain composed of a variable region $V_L$ including an amino acid sequence sufficient to confer specificity for an antigen on the antibody, and a constant region $C_L$, or a fragment of the full-length light chain.

The term "CDR," as used herein, refers to an amino acid sequence which resides in the heavy chain and the light chain hypervariable regions of an immunoglobulin. Each heavy and light chain has three CDRs (CDRH1, CDRH2, CDRH3, and CDRL1, CDRL2, CDRL3). The CDRs provide contact residues that play a major role in the binding of antibodies to antigens or epitopes. As used herein, the term "specifically binding" or "specifically recognizing" has the same meaning as is well known to one of ordinary skill in the art, and indicates that an antibody and an antigen specifically interact with each other to induce an immunological activity.

The term "antigen-binding fragment" refers to a fragment of the whole immunoglobulin structure which possesses a part of a polypeptide responsible for antigen binding. Examples of the antigen-binding fragment useful in the present disclosure include scFv, (scFv)$_2$, scFvFc, Fab, Fab' and F(ab')$_2$, but are not limited thereto.

Of the antigen-binding fragment, Fab is composed of one variable and one constant domain from the light chain, and one variable and the first constant ($C_{H1}$) domain from the heavy chain, retaining one antigen-binding site.

A Fab' fragment is different from Fab in that the Fab' further includes a hinge region having at least one cysteine residue at the C-terminus of the heavy chain $C_{H1}$ domain.

A F(ab')$_2$ fragment forms as two Fab' fragments are joined by a disulfide bond between the cysteine residues of the hinge region. A Fv fragment is a minimal antibody fragment composed only of variable domains from the heavy chain and the light chain. Recombinant techniques for producing the Fv are well known in the art.

In a two-chain Fv fragment, the heavy chain variable domains are associated with the light chain variable domains via a non-covalent bond. A single-chain Fv fragment has a structure in which a heavy chain variable domain and a light chain variable domain are covalently joined to each other via a covalent bond or directly at the C-terminus, so that it can form a dimer as in a two-chain Fv fragment. In this context, the heavy chain variable region and the light chain variable region may be connected with each other through a linker, e.g., a peptide linker, or directly. The peptide linker may be composed of 1 to 100 amino acid residues, or 2 to 50 amino acid residues, with no limitations imposed on the kind of the amino acid residues. For example, the peptide linker may include Gly, Asn and/or Ser, and may also include neutral amino acids such as Thr and/or Ala. Amino acid sequences suitable for use in the peptide linker may be those well known in the art. So long as it has no negative influence on the function of the antigen-binding fragment, the length of the peptide linker may be appropriately adjusted. For example, the peptide linker may be an amino sequence composed of 1 to 100, 2 to 50, or 5 to 25 amino acid residues selected from among Gly, Asn, Ser, Thr, Ala, and a combination thereof. By way of example, the peptide linker may be (G4S)n (wherein n represents the repeating number of (G4S) and may be an integer of 1 to 10, e.g., 2 to 5).

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region that is located between $C_{H1}$ and $C_{H2}$ regions, presenting flexibility to the antigen binding site in an antibody.

When an animal-derived antibody is subjected to chimerization, an animal-derived IgG1 hinge is replaced with a human IgG1 hinge. However, the animal-derived IgG1 hinge is shorter than the human IgG1 hinge, and disulfide bonds between two heavy chains are reduced from 3 to 2, such that differential effects may be elicited from the hinges due to their difference in rigidity. Therefore, modification of a hinge region can increase an antigen binding efficiency of a humanized antibody. Methods of modifying amino acid sequences of hinge regions by deleting, inserting or substituting amino acids are well known to those skilled in the art.

The anti-Annexin A1 antibody may be a monoclonal antibody. Monoclonal antibodies may be prepared using a method well known in the art, for example, a phase display technique.

Meanwhile, individual monoclonal anti-annexin antibodies can be screened on the basis of their Annexin A1 binding capacity using a typical ELISA (Enzyme-Linked ImmunoSorbent Assay) format. They may be analyzed for inhibitory activity using a functional assay, such as competitive ELISA for examining molecular interactions between components within a complex, and cell-based assay. Then, the monoclonal antibody members selected based on potent inhibitory activity may be tested for their respective affinities to Annexin A1 ($K_d$ values).

Since Annexin A1 is known to be overexpressed in cancer or tumor cells and to influence the growth and/or metastasis of cancer, the Annexin A1 antagonist, and/or the anti-annnexin A1 antibody or an antigen-binding fragment thereof according to the present disclosure, which target Annexin A1, can be applied to the diagnosis, prevention and/or treatment of diseases associated with Annexin A1 activation and/or overexpression, such as cancer and immune diseases.

Another embodiment provides a pharmaceutical composition for the prevention and/or treatment of a disease associated with Annexin A1 activation and/or overexpression, including the Annexin A1 antagonist, and/or the anti-Annexin A1 antibody or an antigen-binding fragment thereof as an active ingredient.

Another embodiment provides a method for preventing and/or treating a disease associated with Annexin A1 activation and/or overexpression, including administering the Annexin A1 antagonist, and/or the anti-Annexin A1 antibody or an antigen-binding fragment thereof to a subject in need thereof. The Annexin A1 antagonist, and/or the anti-Annexin A1 antibody or an antigen-binding fragment thereof may be administered in amounts that are pharmaceutically effective, which amount may be determined by the skilled medical practitioner or medical researcher. The prevention and/or treatment method may further include identifying the subject in need of the prevention and/or treatment of the disease before the administration step. The step of identifying may be conducted by any manner and/or methods known to relevant field for identifying whether or not a subject needs the prevention and/or treatment of the disease. For example, the step of identifying may include diagnosing a subject to have the disease, or identifying a subject who is diagnosed as having the disease.

Still another embodiment provides a use of the Annexin A1 antagonist, and/or the anti-Annexin A1 antibody or an antigen-binding fragment thereof in the inhibition of angiogenesis or in the preparation of an angiogenesis inhibitor.

The Annexin A1 antagonist, the anti-Annexin A1 antibody or an antigen-binding fragment thereof, or the pharmaceutical composition according to the present disclosure may be formulated in combination with a pharmaceutically acceptable carrier. Any pharmaceutically acceptable carrier may be contained in the pharmaceutical composition. Examples of the pharmaceutically acceptable carrier available for the pharmaceutical composition of the present disclosure include lactose, dextrose, sucrose, sorbitol, mannitol, starch, gum acacia, calcium phosphate, alginate, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. In addition to the carrier, the pharmaceutical composition may further include a typical additive selected from the group consisting of a diluent, an excipient, a lubricant, a humectant, a sweetener, a flavor enhancer, an emulsifier, a suspending agent, a preservative, and a combination thereof.

The Annexin A1 antagonist, the anti-Annexin A1 antibody or an antigen-binding fragment thereof; or the pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

The content of the anti-Annexin A1 antibody or an antigen-binding fragment thereof in the pharmaceutical composition may be determined in consideration of various factors including the type of formulation the patient's age, weight, and sex, the severity of the disorder being treated, diet, the time of administration, the route of administration, the rate of excretion, and sensitivity. For example, the daily dose of the anti-Annexin A1 antibody or an antigen-binding fragment thereof may be on the order of 0.001 to 1000 mg/kg, particularly on the order of 0.01 to 100 mg/kg, and more particularly on the order of 0.1 to 50 mg/kg, but is not limited thereto. A daily dose may be formulated into a unit dose form or distributed into separate dose forms, or may be included within a multiple dose package.

The term "pharmaceutically effective amount," as used herein, refers to an amount at which the active ingredient (e.g., the anti-Annexin A1 antibody or an antigen-binding fragment thereof) can exert a desired effect, that is, a prophylactic and/or therapeutic effect on a disease associated with Annexin A1 activation and/or overexpression, and may vary depending on various factors including the type of formulation, the patient's age, weight, and sex, the severity of the disorder being treated, diet, the time of administration, the route of administration, the rate of excretion, and sensitivity.

The subject to be administered with the Annexin A1 antagonist, the anti-Annexin A1 antibody or an antigen-binding fragment thereof or the pharmaceutical composition may be a mammal, examples of which include primates such as humans or a monkeys, and rodents such as rats and mice, but are not limited thereto.

The Annexin A1 antagonist, the anti-Annexin A1 antibody or an antigen-binding fragment thereof; or the pharmaceutical composition may be formulated into solutions in oil or aqueous media, suspensions, syrup, emulsions, elixirs, powders, granules, tablets, or capsules, and in this context, a dispersant or a stabilizer may be further employed.

Particularly, the pharmaceutical composition including the anti-Annexin A1 antibody or an antigen-binding fragment thereof can be formulated into immunoliposomes. Liposomes including an antibody can be prepared using methods that are well-known in the art. The immunoliposomes may be produced from a lipid composition including phosphatidylcholine, cholesterol, and PEGylated phosphatidylethanolamine by reverse-phase evaporation. For example, Fab' can be conjugated to liposomes by disulfide reformation.

Capable of specifically binding to Annexin A1 (full-length or extracellular portion (e.g., an N-terminal region)), the Annexin A1 antagonist, or the anti-Annexin A1 antibody or an antigen-binding fragment thereof is applicable to the detection of Annexin A1 or the determination of Annexin A1 activation and/or overexpression.

Accordingly, another embodiment provides a composition for the detection of Annexin A1, including the Annexin A1 antagonist, and/or the anti-Annexin A1 antibody or an antigen-binding fragment thereof. Another embodiment provides a method for detecting Annexin A1, including applying the Annexin A1 antagonist and/or the anti-Annexin A1 antibody or an antigen-binding fragment thereof to a biological sample; and measuring an antigen-antibody reaction (binding) in the biological sample. In the detecting method, Annexin A1 is determined to exist in the biological sample if the antigen-antibody reaction occurs. Another embodiment provides a use of the Annexin A1 antagonist and/or the anti-Annexin A1 antibody or an antigen-binding fragment thereof in detecting Annexin A1. The biological sample may be selected from among cells, tissues, and body fluids (e.g., blood, serum, etc.) isolated from mammals including primates such as humans and monkeys, and rodents such as mice and rats. The detection of Annexin A1 is accounted for by examining whether and to what extent Annexin A1 exists and is expressed.

Another embodiment provides a pharmaceutical composition for determining Annexin A1 activation and/or overexpression, and/or diagnosing a disease associated with activation and/or overexpression of Annexin A1, including the Annexin A1 antagonist, and/or the anti-Annexin A1 antibody or an antigen-binding fragment thereof. Another embodiment provides a method for determining Annexin A1 activation and/or overexpression, and/or diagnosing a disease associated with Annexin A1 activation and/or overexpression, including applying the Annexin A1 antagonist and/or the anti-Annexin A1 antibody or an antigen-binding fragment thereof to a biological sample from a subject; and measuring an antigen-antibody reaction (binding) in the biological sample. In this method, the biological sample or the subject from which the biological sample is obtained is determined to have Annexin A1 activation and/or overexpression or a disease associated with Annexin A1 activation and/or overexpression if the antigen-antibody reaction in the biological sample occurs at a higher level than that in a normal sample (or a negative control) (e.g., a sample free of a disease associated with activation and/or overexpression of Annexin A1 or free of Annexin A1 activation and/or overexpression, such as a biological sample from a subject known to be free of the disease).

Accordingly, the method may further include applying the Annexin A1 antagonist and/or the anti-Annexin A1 antibody or an antigen-binding fragment thereof to a normal sample, and measuring an antigen-antibody reaction (binding) in the normal sample. The biological sample may be selected from among cells, tissues, and body fluids (e.g., blood, serum, etc.) isolated from a subject, for instance, a subject suspected to have a disease associated with Annexin A1 expression. The normal sample (or a negative control) may be selected from among cells, tissues, and body fluids (e.g., blood, serum, etc.) obtained (isolated) from a subject which is identified as being free of Annexin A1 activation and/or overexpression, and/or a disease associated with Annexin A1 activation and/or overexpression. The subject may be a mammal selected from among primates including humans and monkeys, and rodents including mice and rats.

The examination of the biological sample for an antigen-antibody reaction may be carried out using a method well known in the art, for example, on the basis of an enzyme reaction, fluorescence, luminescence, and/or radiation. Examples of the method useful for examining the antigen-antibody reaction of the biological sample may include immune-chromatography, immunohistochemistry, enzyme linked immunosorbent assay (ELISA), radioimmunoassay (RIA), enzyme immunoassay (EIA), fluorescence immunoassay (FIA), luminescence immunoassay (LIA), and Western blotting, but are not limited thereto.

The disease associated with Annexin A1 activation and/or overexpression may be selected from the group consisting of cancers, cancer metastasis, inflammatory diseases (e.g., inflammation), immune system diseases, and the like, and for example, cancer and/or cancer metastasis. For example, the immune system disease may be selected from the group consisting of a TNF signaling-related disease, or an autoimmune disease, as exemplified by asthma, atopic dermatitis, rheumatoid arthritis, allergy, psoriasis, vitiligo, Graves' disease, glomerulonephritis, diabetes (e.g., insulin-dependent diabetes (type 1 diabetes mellitus)), multiple sclerosis, thyroiditis, anemia (e.g., pernicious anemia), systemic lupus erythematosus, sepsis, and the like. The cancer may be one characterized by overexpression of Annexin A1, and may be a solid cancer or a blood cancer. The cancer may be selected from the group consisting of squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and a combination thereof. The cancer may be a primary cancer or a metastatic cancer.

A still additional aspect provides a polynucleotide encoding a polypeptide, antibody, or antibody fragment described herein, for instance, a polypeptide, antibody, or antibody fragment which comprises at least one selected from among amino acid sequences set forth in SEQ ID NO: 1 to SEQ ID NO: 150. In one embodiment, the polynucleotide may encode a polypeptide having one selected from among amino acid sequences set forth in SEQ ID NO: 137 to SEQ ID NO: 146. A still another additional aspect of the present disclosure provides a recombinant vector carrying the polynucleotide. Also, contemplated in accordance with a still further additional aspect of the present disclosure is a recombinant cell transformed with the recombinant vector.

The term "vector" refers to a means for expressing a target gene in a host cell, as exemplified by a plasmid vector, a cosmid vector, and a viral vector such as a bacteriophage vector, adenovirus vector, retrovirus vector, and an adeno-related virus vector. The recombinant vector may be constructed from, but not limited to, well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by manipulation.

In the recombinant vector, the polynucleotide may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be constructed typically as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a pLλ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, or a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed in the present disclosure. Examples of the prokaryotic host cell available for the present disclosure include *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens* and various *Pseudomonas* species. Eukaryotic host cells to be transformed may be *Saccharomyce cerevisiae*, insect cells, and animal cells including, but not limited to Sp2/0, CHO (Chinese hamster ovary) K1, CHO DG44, PER.C6, W138, BHK, COS-7, 293, HepG2, Huh7, 3T3, RIN, and MDCK.

Using a method well known in the art, the polynucleotide or a recombinant vector carrying the polynucleotide may be introduced (incorporated) into a host cell. This transformation may be carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

Binding to an extracellular portion of Annexin A1, the polypeptide of the present disclosure is applicable to a diagnosis system of Annexin A1-related diseases through the quantification and imaging analysis of Annexin A1, and useful in the development of a therapeutic targeting Annexin A1.

Hereafter, the present disclosure will be described in detail by examples.

The following examples are intended merely to illustrate the disclosure and are not to be construed in a way that limits the disclosure.

EXAMPLE 1

Annexin A1-Binding Polypeptide Library Analysis

To screen Annexin A1-binding scFv-type antibodies, a biopanning process was conducted with an antibody phage library. In this context, a peptide consisting of 30 amino acids (MAMVSEFLKQAWFIENEEQEYVQTVKSSKG; SEQ ID NO: 151) corresponding to an N terminal region of Annexin A1 was synthesized in a biotin conjugated form. As for a full-length Annexin A1 protein (a total of 346 amino acids; Accession No. NP_000691.1; SEQ ID NO: 152), its coding DNA fragment was digested with the restriction enzymes NdeI and XhoI (NEB, R0146S), inserted into a pET21b vector (Novagen), expressed in *E. coli* BL21 (Invitrogen), followed by purification with a His tag and then biotinylation with a kit (Pierce) to give a biotnylated protein.

```
Annexin A1 full-length sequence
                                (346a.a.; SEQ ID NO: 152)
mamvseflkq awfieneeqe yvqtvksskg gpgsavspyp tfnpssdvaa lhkaimvkgv deatiidilt krnnaqrqqi kaaylqetgk pldetlkkal tghleevvla llktpaqfda delraamkgl gtdedtliei lasrtnkeir dinrvyreel krdlakdits dtsgdfrnal lslakgdrse dfgvnedlad sdaralyeag errkgtdvnv fntilttrsy pqlrrvfqky tkyskhdmnk vldlelkgdi ekcltaivkc atskpaffae klhqamkgvg trhkalirim vsrseidmnd ikafyqkmyg islcqailde tkgdyekilv alcggn
```

Each of the Biotinylated Annexin A1 N-terminal peptide and the full-length Annexin A1 protein was captured by streptavidin-coated magnetic beads (Invitrogen), and then allowed to bind to an scFv-displaying phage library ($10^{12}$ pfu; constructed with reference to 'Construction of a large synthetic human scFv library with six diversified CDRs and high functional diversity. Moll. Cells 27, 225-235, Feb. 28, 2009') by incubation at 4° C. for 30 min. This biopanning process for recovering Annexin A1-binding scFv (Ehrlich G K, Berthold W, and Bailon P. *Phage display technology. Affinity selection by biopanning*. Methods in Molecular Biology. 2000. 147:195-208), and subsequently removing unbound scFv with a washing buffer HBSS(+) (Gibco) was performed 4 and 3 rounds, respectively, for the N-terminal region and the full-length protein. As a result, scFv pools which specifically bind to the Annexin A1 N-terminal region and the full-length Annexin A1 protein, respectively, were obtained.

In order to analyze respective scFv pools which specifically bind to the Annexin A1 N-terminal peptide and the full-length Annexin A1 protein, ER2537 (New England Biolabs Inc) to which individual phage clones were infected was incubated, and cytoplasmic fractions were separated using a 20% (w/v) sucrose solution to obtain scFv displayed on phage surfaces was obtained.

To confirm the binding of the scFv to the full-length Annexin A1, the full-length Annexin A1 protein was applied in an amount of 4 ug (microgram) per well to 96-well immunoplates (Nunc) to which the cytoplasmic fraction containing the scFv was then added. For the binding confirmation of the Annexin A1 N-terminus (SEQ ID NO: 151), the biotinylated N-terminal peptide (SEQ ID NO: 151; Peptron) was applied in an amount of 1 nmol per well to streptavidin-coated 96-well plates (NUNC) before the cytoplasmic fraction containing the scFv.

In the plates, the fractions were incubated at room temperature for 1 hr with an anti-HA-HRP antibody (Santa Cruz), which can detect the HA tag attached to the scFv, and then reacted at room temperature for 10 min with a Super AquaBlue ELISA substrate solution (eBioScience) for the HRP conjugated to the anti-HA antibody. Absorbance was read at 405 nm to determine the binding of scFv to Annexin A1. Separately, negative control immunoplates coated with a mock protein were treated with the same cytoplasmic fractions. A difference between the test immunoplates and the negative controls allowed for the selection of only the scFv specifically binding to Annexin A1.

The results are depicted in FIGS. 1 to 4.

FIG. 1 shows ELISA analysis results of the scFv pool binding to the N-terminal region consisting of 30 amino acids (MAMVSEFLKQAWFIENEEQEYVQTVKSSKG; SEQ ID NO: 151) after 3 rounds of the biopanning process. Compared to the mock-coated immunoplate as a negative control, individual phage clones with higher ELISA signal intensities were observed on the Annexin A1 N-terminal peptide-coated immunoplate.

Figure 2:
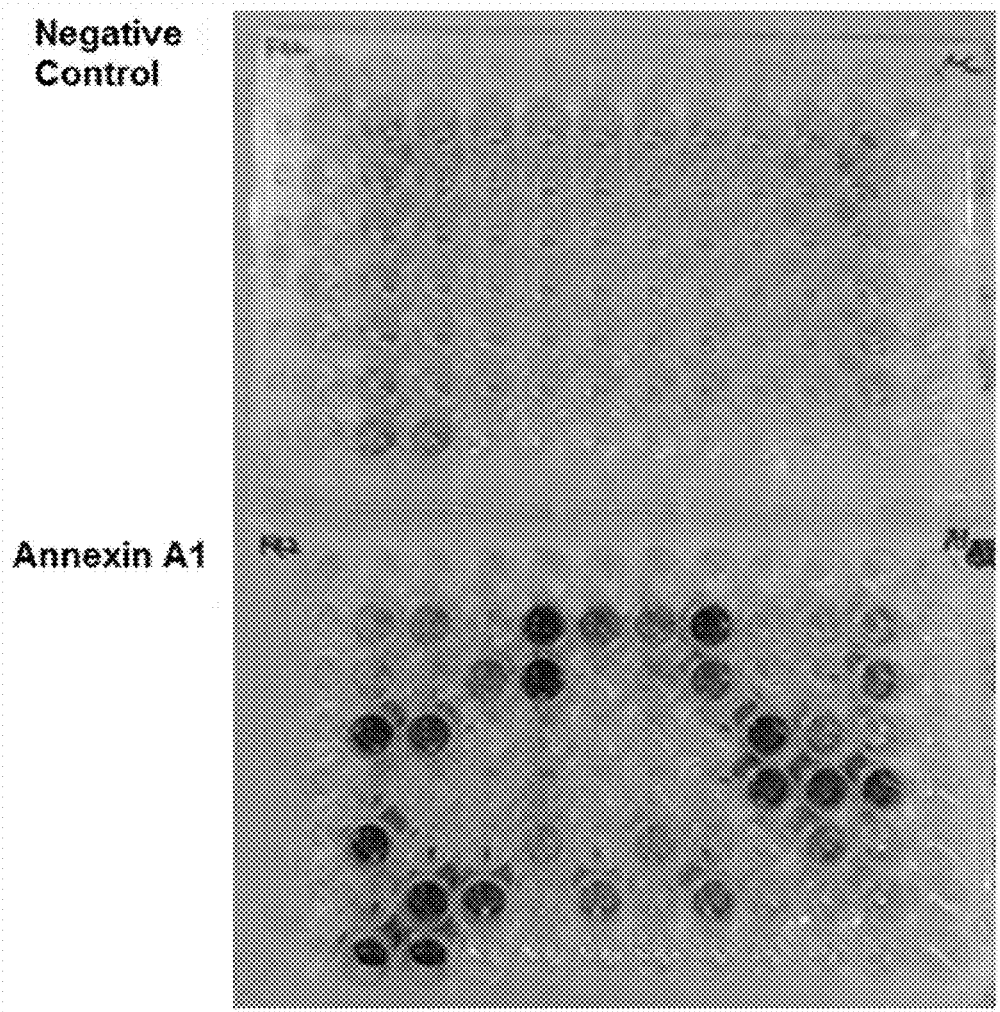
FIG. 2 is an image showing ELISA analysis results for the scFv pool binding to the full-length Annexin A1 obtained after 4 rounds of the biopanning process.

FIG. 2 shows ELISA analysis results of the scFv pool binding to the full-length Annexin A1 (a total of 346 amino acids, Accession No. NP_000691.1; SEQ ID NO: 152) after 4 rounds of the biopanning process. Compared to the mock-coated immunoplate as a negative control, individual phage clones with higher ELISA signal intensities were observed on the Annexin A1-coated immunoplate.

Figure 3:
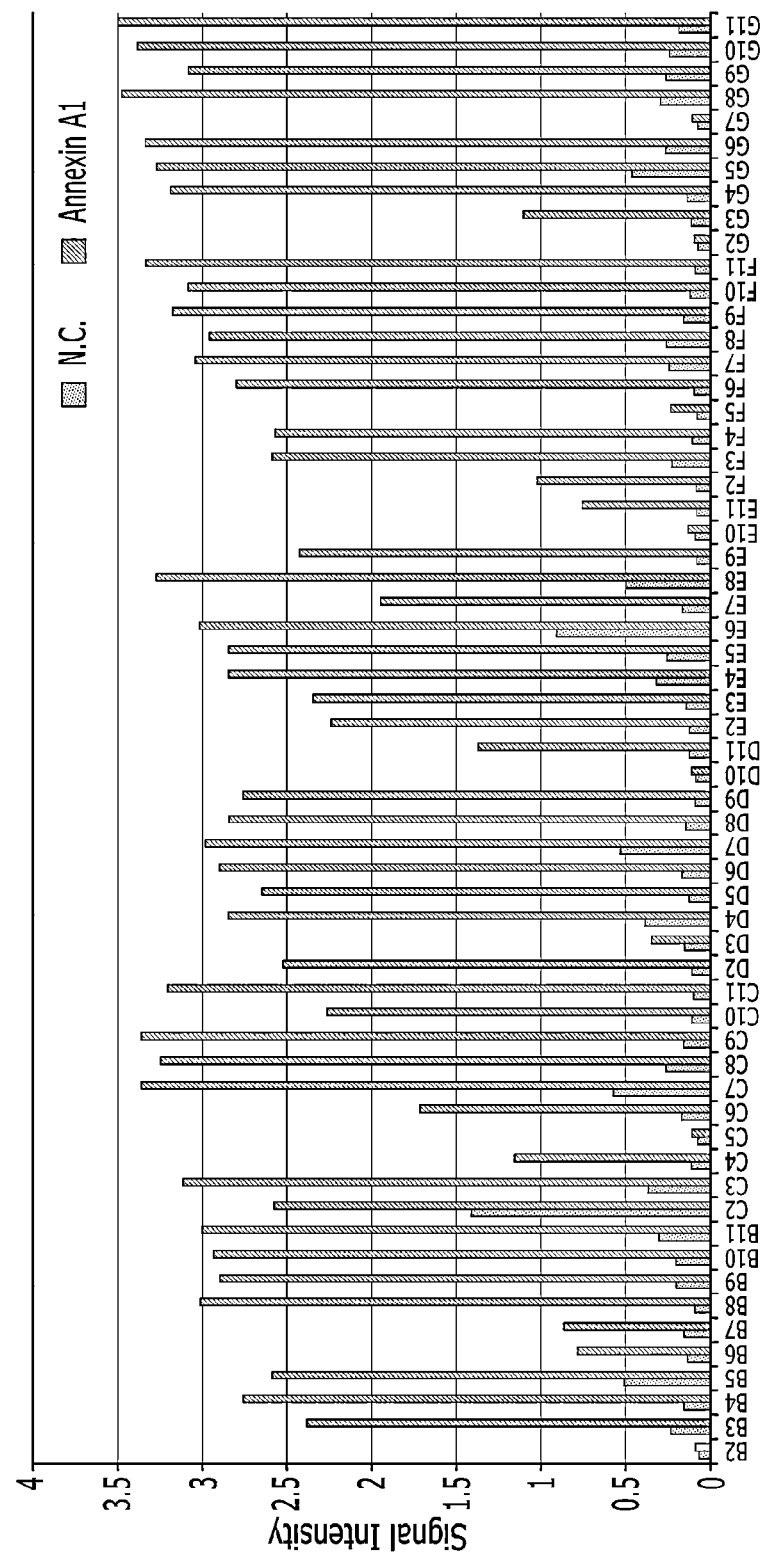
FIG. 3 is a graph showing the signal intensities observed in FIG. 1 (scFv binding to Annexin A1 N-terminus) as numerical values.
Figure 4:
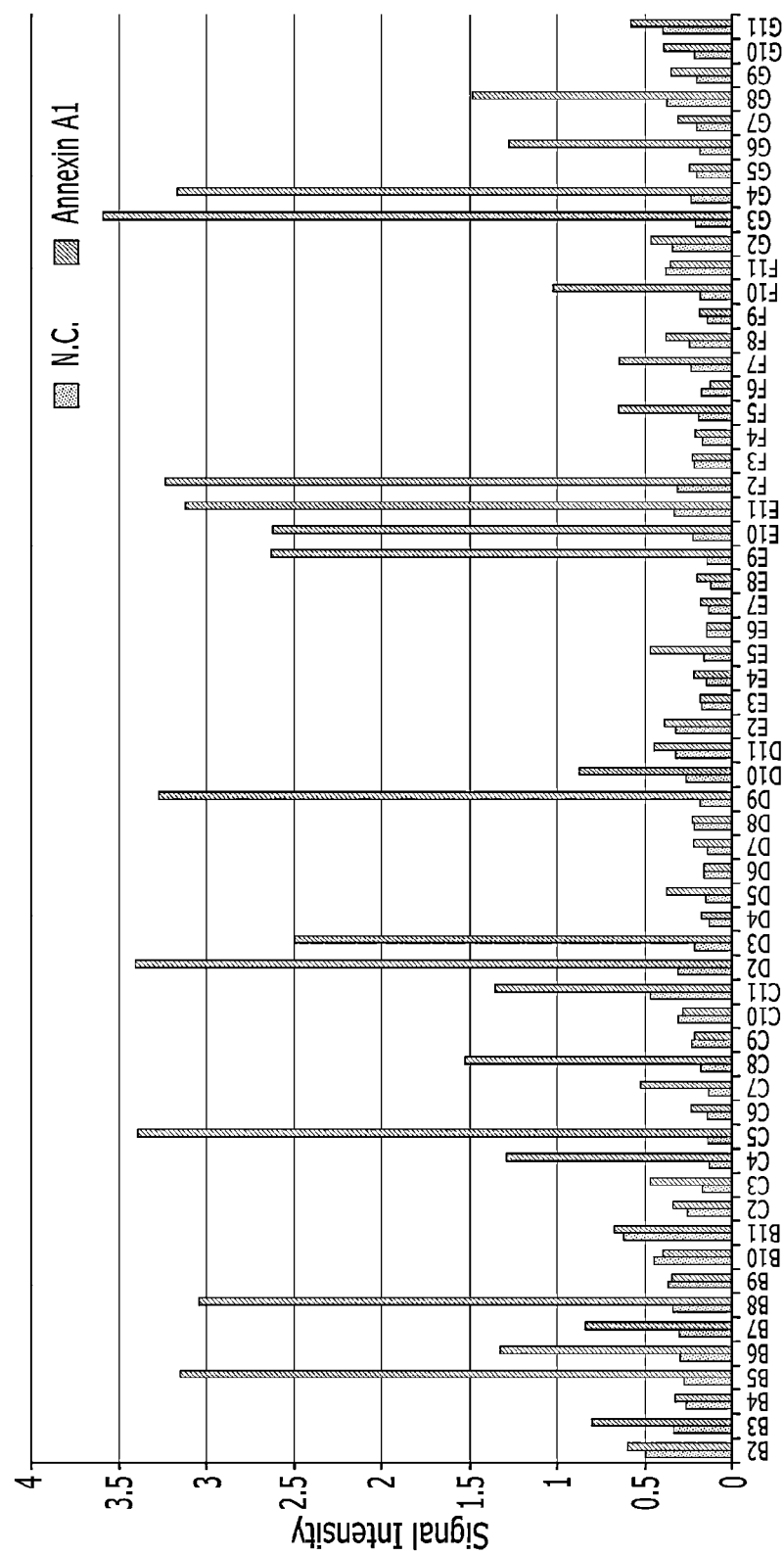
FIG. 4 is a graph showing the signal intensities observed in FIG. 2 (scFv binding to full-length Annexin A1) as numerical values.

FIGS. 3 and 4 are graphs showing the signal intensities observed in FIGS. 1 (scFv binding to Annexin A1 N-terminus) and 2 (scFv binding to full-length Annexin A1) as numerical values.

EXAMPLE 2

Sequence Analysis of Annexin A1-Binding Polypeptides

The scFv selected through ELISA was subjected to sequence analysis. A DNA sequence was amplified from *E. coli* stock of each scFv by PCR using the following PCR primers (Genotech). DNA base sequencing for the PCR products thus obtained were conducted with the following sequencing primers (Genotech).

```
PCR primer
PC3X forward primer:
                                    (SEQ ID NO: 153)
5'-GCACGACAGGTTTCCCGAC-3'

PC3X Reverse primer:
                                    (SEQ ID NO: 154)
5'-AACCATCGATAGCAGCACCG-3'

Sequencing primer
                                    (SEQ ID NO: 155)
5'-AAGACAGCTATCGCGATTGCAG-3'
```

Amino acid sequences thus obtained are listed in Tables 3 to 6.

TABLE 3

Heavy chain complementarity determining region of scFv binding to N-terminus of Annexin A1

| Antibody | CDR-H1 | CDR-H2 | CDR-H3 |
|---|---|---|---|
| N31 | NYAMS (SEQ ID NO: 1) | AISPGDSNT (SEQ ID NO: 12) | RMTKRFDY (SEQ ID NO: 43) |
| N32 | NYAMS (SEQ ID NO: 1) | GIYPNSGSNT (SEQ ID NO: 13) | RRPTLFDY (SEQ ID NO: 44) |
| N33 | DYSMG (SEQ ID NO: 2) | GIYPSGGNT (SEQ ID NO: 14) | RKPTIFDY (SEQ ID NO: 45) |
| N34 | NYAMS (SEQ ID NO: 1) | AIYPGGGSI (SEQ ID NO: 15) | RRLQIFDY (SEQ ID NO: 46) |
| N35 | GYSMS (SEQ ID NO: 3) | GIYSGDSSK (SEQ ID NO: 16) | RSLSIFDY (SEQ ID NO: 47) |
| N36 | NYAMS (SEQ ID NO: 1) | GISSDDGSKY (SEQ ID NO: 17) | ARTLTIFDY (SEQ ID NO: 48) |
| N37 | DYAMS (SEQ ID NO: 4) | GIYPSSSSK (SEQ ID NO: 18) | KRLALFDY (SEQ ID NO: 49) |
| N38 | NYAMS (SEQ ID NO: 1) | GISSDNSSKY (SEQ ID NO: 19) | RRISLFDY (SEQ ID NO: 50) |
| N39 | GYSMS (SEQ ID NO: 3) | GIYYGDGST (SEQ ID NO: 20) | RRATLFDY (SEQ ID NO: 51) |
| N311 | NYAMS (SEQ ID NO: 1) | AIYPGNGSK (SEQ ID NO: 21) | KGLSLFDY (SEQ ID NO: 52) |
| N314 | GYAMS (SEQ ID NO: 5) | GIYPGGGST (SEQ ID NO: 22) | RRLTIFDY (SEQ ID NO: 53) |
| N43 | DYSMG (SEQ ID NO: 2) | GIYPSGGNT (SEQ ID NO: 14) | KRPSRFDY (SEQ ID NO: 54) |
| N44 | GYSMS (SEQ ID NO: 3) | GIYPGGSST (SEQ ID NO: 23) | KRPTLFDY (SEQ ID NO: 55) |
| N45 | DYAMS (SEQ ID NO: 4) | AIYPDGGST (SEQ ID NO: 24) | KRITLFDY (SEQ ID NO: 56) |
| N46 | SYAMS (SEQ ID NO: 6) | GIYPSDGNI (SEQ ID NO: 25) | KNKAPFDY (SEQ ID NO: 57) |

TABLE 3-continued

Heavy chain complementarity determining region of scFv binding to N-terminus of Annexin A1

| Antibody | CDR-H1 | CDR-H2 | CDR-H3 |
|---|---|---|---|
| N48 | DYAMS (SEQ ID NO: 4) | GIYPSSSSK (SEQ ID NO: 18) | KRLALFDY (SEQ ID NO: 49) |
| N49 | NYAMS (SEQ ID NO: 1) | AIYPSNGSK (SEQ ID NO: 26) | KGLSLFDY (SEQ ID NO: 52) |

TABLE 4

Light chain complementarity determining region of scFv binding to N-terminus of Annexin A1

| Antibody | CDR-L1 | CDR-L2 | CDR-L3 |
|---|---|---|---|
| N31 | SGSSSNIGSNDVT (SEQ ID NO: 75) | DNSK (SEQ ID NO: 95) | GTWDDSLNG (SEQ ID NO: 113) |
| N32 | TGSSSNIGSNSVN (SEQ ID NO: 76) | SDSH (SEQ ID NO: 96) | ATWDDSLNG (SEQ ID NO: 114) |
| N33 | SGSSSNIGNNDVN (SEQ ID NO: 77) | SNSH (SEQ ID NO: 97) | GTWDDSLNG (SEQ ID NO: 113) |
| N34 | TGSSSNIGSNNVT SEQ ID NO: 78) | SDSH (SEQ ID NO: 96) | GSWDYSLSA (SEQ ID NO: 115) |
| N35 | SGSSSNIGSNAVT (SEQ ID NO: 79) | SNSQ (SEQ ID NO: 98) | GTWDYSLSG (SEQ ID NO: 116) |
| N36 | SGSSSNIGSNNVT (SEQ ID NO: 80) | SDSH (SEQ ID NO: 96) | GTWDYSLSG (SEQ ID NO: 116) |
| N37 | SGSSSNIGNNAVN (SEQ ID NO: 81) | SNSH (SEQ ID NO: 97) | GAWDYSLSG (SEQ ID NO: 117) |
| N38 | TGSSSNIGSNNVT (SEQ ID NO: 78) | SDSH (SEQ ID NO: 96) | GSWDYSLSA (SEQ ID NO: 115) |
| N39 | TGSSSNIGSNSVS (SEQ ID NO: 82) | SDNH (SEQ ID NO: 99) | GTWDYSLSG (SEQ ID NO: 116) |
| N311 | TGSSSNIGSNNVT (SEQ ID NO: 78) | SDSH (SEQ ID NO: 96) | GAWDYSLNA (SEQ ID NO: 118) |
| N314 | SGSSSNIGNNDVT (SEQ ID NO: 83) | SDSH (SEQ ID NO: 96) | GTWDDSLSG (SEQ ID NO: 119) |
| N43 | TGSSSNIGNNDVN (SEQ ID NO: 84) | SNSH (SEQ ID NO: 97) | GTWDDSLNG (SEQ ID NO: 113) |
| N44 | TGSSSNIGSNNVT (SEQ ID NO: 78) | ADSN (SEQ ID NO: 100) | GTWDDSLSA (SEQ ID NO: 120) |

TABLE 4-continued

Light chain complementarity determining region of scFv binding to N-terminus of Annexin A1

| Antibody | CDR-L1 | CDR-L2 | CDR-L3 |
|---|---|---|---|
| N45 | TGSSSNIGSNNVT (SEQ ID NO: 78) | SDSH (SEQ ID NO: 96) | GTWDYSLSG (SEQ ID NO: 116) |
| N46 | TGSSSNIGNNTVS (SEQ ID NO: 85) | SDSH (SEQ ID NO: 96) | ATWDDSLNA (SEQ ID NO: 121) |
| N48 | SGSSSNIGNNAVN (SEQ ID NO: 81) | SNSH (SEQ ID NO: 97) | GAWDYSLSG (SEQ ID NO: 117) |
| N49 | TGSSSNIGSNNVT (SEQ ID NO: 78) | SDSH (SEQ ID NO: 96) | GAWDYSLNG (SEQ ID NO: 122) |

TABLE 5

Heavy chain complementarity determingin region of scFv binding to full-length Annexin A1

| Antibody | CDR-H1 | CDR-H2 | CDR-H3 |
|---|---|---|---|
| F2 | NYSMS (SEQ ID NO: 7) | GISSDGGNK (SEQ ID NO: 27) | RRAPIPFDY (SEQ ID NO: 58) |
| F4 | GYYMS (SEQ ID NO: 8) | SISPSGSSI (SEQ ID NO: 28) | KGSPGFDY (SEQ ID NO: 59) |
| F5 | DYAMS (SEQ ID NO: 4) | GISYGGGNT (SEQ ID NO: 29) | KRLGSFDY (SEQ ID NO: 60) |
| F6 | NYAMS (SEQ ID NO: 1) | SISSNSGNK (SEQ ID NO: 30) | KATLGMDHIHAYSAYGMDV (SEQ ID NO: 61) |
| F8 | SYSMS (SEQ ID NO: 9) | GISPGSGSI (SEQ ID NO: 31) | RRIHPFDY (SEQ ID NO: 62) |
| F10 | DYSMS (SEQ ID NO: 10) | VISPDSSNT (SEQ ID NO: 32) | KVTGTCGPRSCYYYDAMDV (SEQ ID NO: 63) |
| 31 | DYSMS (SEQ ID NO: 10) | SISPDGGNK (SEQ ID NO: 33) | KRTTLFDY (SEQ ID NO: 64) |
| 32 | NYSMS (SEQ ID NO: 7) | GISPDGGSI (SEQ ID NO: 34) | RRSSLFDY (SEQ ID NO: 65) |
| 34 | GYYMS (SEQ ID NO: 8) | SISPSGSSI (SEQ ID NO: 28) | KGSPGFDY (SEQ ID NO: 59) |
| 35 | NYSMS (SEQ ID NO: 7) | GISPDDGSI (SEQ ID NO: 35) | RRVGLFDY (SEQ ID NO: 66) |
| 36 | SYYMS (SEQ ID NO: 11) | LISPGSGSI (SEQ ID NO: 36) | RSISGRQYANPSYDDAMDV (SEQ ID NO: 67) |
| A1 | SYSMS (SEQ ID NO: 9) | GISPNGGSI (SEQ ID NO: 37) | KRAALFDY (SEQ ID NO: 68) |

TABLE 5-continued

Heavy chain complementarity determingin region of scFv binding to full-length Annexin A1

| Antibody | CDR-H1 | CDR-H2 | CDR-H3 |
|---|---|---|---|
| A4 | NYSMS (SEQ ID NO: 7) | AISSSGGST (SEQ ID NO: 38) | RRGNLFDY (SEQ ID NO: 69) |
| A5 | SYYMS (SEQ ID NO: 11) | LISPGSGSI (SEQ ID NO: 36) | KGGPARRASTFDY (SEQ ID NO: 70) |
| A6 | NYSMS (SEQ ID NO: 7) | SISPSSGSI (SEQ ID NO: 39) | KRNWTFDY (SEQ ID NO: 71) |
| A8 | NYSMS (SEQ ID NO: 7) | LISPDSSSI (SEQ ID NO: 40) | KRATVFDY (SEQ ID NO: 72) |
| A10 | NYAMS (SEQ ID NO: 1) | SISYGNSNK (SEQ ID NO: 41) | RAPGPFNY (SEQ ID NO: 73) |
| A11 | NYSMS (SEQ ID NO: 7) | AISSDGGST (SEQ ID NO: 42) | RRGALFDY (SEQ ID NO: 74) |

TABLE 6

Light chain complementarity determining region of scFv binding to full-length Annexin A1

| Antibody | CDR-L1 | CDR-L2 | CDR-L3 |
|---|---|---|---|
| F2 | TGSSSNIGSNAVS (SEQ ID NO: 86) | YNSQ (SEQ ID NO: 101) | GAWDDSLNA (SEQ ID NO: 123) |
| F4 | SGSSFNIGSNDVS (SEQ ID NO: 87) | SDSH (SEQ ID NO: 96) | GSWDYSLSA (SEQ ID NO: 115) |
| F5 | TGTSSNIGSNYVS (SEQ ID NO: 88) | AGNH (SEQ ID NO: 102) | GSWDSSLSA (SEQ ID NO: 124) |
| F6 | TGSSSNIGSNSVS (SEQ ID NO: 82) | ANSN (SEQ ID NO: 103) | AAWDDSLNA (SEQ ID NO: 125) |
| F8 | TGSSSNIGNNDVS (SEQ ID NO: 89) | SDNQ (SEQ ID NO: 104) | GAWDSSLNA (SEQ ID NO: 126) |
| F10 | SGSSSNIGSNAVS (SEQ ID NO: 90) | YNSH (SEQ ID NO: 105) | ATWDSSLNG (SEQ ID NO: 127) |
| 31 | TGSSSNIGSNDVS (SEQ ID NO: 91) | DNSQ (SEQ ID NO: 106) | AAWDASLSA (SEQ ID NO: 128) |
| 32 | TGSSSNIGNNSVT (SEQ ID NO: 92) | DSQR (SEQ ID NO: 107) | GSWDASLSA (SEQ ID NO: 129) |
| 34 | SGSSFNIGSNDVS (SEQ ID NO: 87) | SDSH (SEQ ID NO: 96) | GSWDYSLSA (SEQ ID NO: 115) |
| 35 | TGSSSNIGNNDVS (SEQ ID NO: 89) | YDNQ (SEQ ID NO: 108) | GAWDASLSA (SEQ ID NO: 130) |
| 36 | SGSSSNIGSNNVT (SEQ ID NO: 80) | ANSN (SEQ ID NO: 103) | GAWDDSLSG (SEQ ID NO: 131) |
| A1 | SGSSSNIGSNDVT (SEQ ID NO: 75) | YDSN (SEQ ID NO: 109) | GAWDYSLNG (SEQ ID NO: 122) |
| A4 | TGSSSNIGSNDVS (SEQ ID NO: 91) | DDSN (SEQ ID NO: 110) | GSWDASLNG (SEQ ID NO: 132) |
| A5 | SGSSFNIGSNDVS (SEQ ID NO: 87) | DNSK (SEQ ID NO: 111) | GSWDDSLSG (SEQ ID NO: 133) |
| A6 | TGSSSNIGNNDVS (SEQ ID NO: 89) | SDNQ (SEQ ID NO: 104) | GAWDSSLNA (SEQ ID NO: 126) |
| A8 | SGSSSNIGSNDVS (SEQ ID NO: 93) | YDSN (SEQ ID NO: 109) | GTWDSSLSG (SEQ ID NO: 134) |
| A10 | TGSSSNIGINDVS (SEQ ID NO: 94) | ADNN (SEQ ID NO: 112) | AACDDNLND (SEQ ID NO: 135) |
| A11 | TGSSSNIGNNDVS (SEQ ID NO: 89) | YNSQ (SEQ ID NO: 101) | GSWDDSLSA (SEQ ID NO: 136) |

Four and six representative samples selected, respectively, from the base sequenced Annexin A1 N terminus-binding scFv and full-length Annexin A1-binding scFv were subjected to full-length base sequencing. All frameworks of the scFv given in Tables 3 to 6, except for CDR, are the same as in the representative samples. The full-length base sequencing results are given in Tables 7 and 8, and FIG. 5.

TABLE 7

Amino acid sequence of scFv binding to N-terminus of Annexin A1

| Antibody | Amino acid sequence of scFv |
|---|---|
| N32 | EVQLLESGGG LVQPGGSLRL SCAASGFTFS NYAMSWVRQA PGKGLEWVSG IYPNSGSNTY YADSVKGRFT ISRDNSKNTL YLQMNSLRAE DTAVYYCARR PTLFDYWGQG TLVTVGSGGG GSGGGGSGGG GSQSVLTQPP SASGTPGQRV TISCTGSSSN IGSNSVNWYQ QLPGTAPKLL IYSDSHRPSG VPDRFSGSKS GTSASLAISG LQSEDEADYY CATWDDSLNG YVFGGGTKLT VLG (SEQ ID NO: 137) |
| N34 | EVQLLESGGG LVQPGGSLRL SCAASGFTFS NYAMSWVRQA PGKGLEWVSA IYPGGGSIYY ADSVKGRFTI SRDNSKNTLY LQMNSLRAED TAVYYCARRL QIFDYWGQGT LVTVSSGGGG SGGGGSGGGG GSQSVLTQPPS ASGTPGQRVT ISCTGSSSNI GSNNVTWYQQ LPGTAPKLLI YSDSHRPSGV PDRFSGSKSG TSASLAISGL QSEDEADYYC GSWDYSLSAY VFGGGTKLTV LG (SEQ ID NO: 138) |

TABLE 7-continued

Amino acid sequence of scFv binding to N-terminus of Annexin A1

| Antibody | Amino acid sequence of scFv |
|---|---|
| N314 | EVQLLESGGG LVQPGGSLRL SCAASGFTFG GYAMSWVRQA<br>PGKGLEWVSG IYPGGGSTYY ADSVKGRFTI SRDNSKNTLY<br>LQMNSLRAED TAVYYCARRL TIFDYWGQGT LVTVSSGGGG<br>SGGGGSGGGG SQSVLTQPPS ASGTPGQRVT ISCSGSSSNI<br>GNNDVTWYQQ LPGTAPKLLI YSDSHRPSGV PDRFSGSKSG<br>TSASLAISGL RSEDEADYYC GTWDDSLSGY VFGGGTKLTV<br>LG<br>(SEQ ID NO: 139) |
| N43 | EVQLLESGGG LVQPGGSLRL SCAASGFTFS DYSMGWVRQA<br>PGRGLEWVSG IYPSGGNTYY ADSVKGRFTI SRDNSKNTLY<br>LQMNSLRAED TAVYYCAKRP SRFDYWGQGT LVAVSSGGGG<br>SGGGGSGGGG SQSVLTQPPS ASGTPGQRVT ISCTGSSSNI<br>GNNDVNWYQQ LPGTAPKLLI YSNSHRPSGV PDRFSGSKSG<br>TSASLAISGL RSEDEADYYC GTWDDSLNGY VFGGGTKLTV<br>LG<br>(SEQ ID NO: 140) |

TABLE 8

Amino acid sequence of scFv binding to full-length Annexin A1

| Antibody | Amino acid sequence of scFv |
|---|---|
| F2 | EVQLLESGGG LVQPGGSLRL SCAASGFTFS NYSMSWVRQA<br>PGKGLEWVSG ISSDGGNKYY ADSVKGRFTI SRDNSKNTLY<br>LQMNSLRAED TAVYYCARRA IPFDYWGQGT LVTVSSGGGG<br>SGGGGSGGGG SQSVLTHPPS ASGTPGQRVT ISCTGSSSNI<br>GSNAVSWYQQ LPGTAPKLLI YYNSQRPSGV PDRFSGSKSG<br>TSASLAISGL RSEDEADYYC GAWDDSLNAY VFGGGTKLTV<br>LG<br>(SEQ ID NO: 141) |
| F4 | EVQLLESGGG LVQPGGSLRL SCAASGFTFS GYYMSWVRQA<br>PGKGLEWVSS ISPSGSSIYY ADSVKGRFTI SRDNSKNTLY<br>LQMNSLRAED TAVYYCAKGS PGFDYWGQGT LVTVSSGGGG<br>SGGGGSGGGG SQSVLTQPPS ASGAPGQRVT ISCSGSSFNI<br>GSNDVSWYQQ LPGTAPKLLI YSDSHRPSGV PDRFSGSKSG<br>TSASLAISGL QSEDEADYYC GSWDYSLSAY VFGGGTKLTV<br>LG<br>(SEQ ID NO: 142) |
| F5 | EVQLLESGGG LVQPGGSLRL SCAASGFTFS DYAMSWVRQA<br>PGKGLEWVSG ISYGGGNTYY ADSVKGRFTI SRDNSKNTLY<br>LQMNSLRAED TAVYYCAKRL GSFDYWGQGT LVTVSSGGGG<br>SGGGGSGGGG SQSVLTQPPS ASGTPGRRVT ISCTGTSSNI<br>GSNYVSWYRQ LPGTAPKLLI YAGNHRPSGV PDRFSGSKSG<br>TSASLAISGL RSEDEADYYC GSWDSSLSAY VFGGGTKLTV<br>LG<br>(SEQ ID NO: 143) |
| F6 | EVQLLESGGG LVQPGGSLRL SCAASGFTFS NYAMSWVRQA<br>PGKGLEWVSS ISSNSGNKYY ADSVKGRFTI SRDNSKNTLY<br>LQMNSLRAED TAVYYCAKAT LGMDHIHAYS AYGMDVWGQG<br>TLVTVSSGGG GSGGGSGGG GSQSVLTQPP SASGTPGQRA<br>TISCTGSSSN IGSNSVSWYQ QLPGTAPKLL IYANSNRPSG<br>VPDRFSGSKS GTSASLAISG LRSEDEADYY CAAWDDSLNA<br>YVFGGGTKLT VLG<br>(SEQ ID NO: 144) |
| F8 | EVQLLESGGG LVQPGGSLRL SCAASGFTFS SYSMSWVRQA<br>PGKGLEWVSG ISPGSGSIYY ADSVKGRFTI SRDNSKNTLY<br>LQMNSLRAED TAVYYCARRI HPFDYWGQGT LVAVSSGGGG<br>SGGGGSGGGG SQSVLTQPPS ASGTPGQRVT ISCTGSSSNI<br>GNNDVSWYQQ LPGTAPKLLI YSDNQRPSGV PGRFSGSKSG<br>TSASLAISGL RSEDEADYYC GAWDSSLNAY VFGGGTKLTV<br>LG<br>(SEQ ID NO: 145) |
| F10 | EVQLLESGGG LVQPGGSLRL SCAASGFTFS DYSMSWVRQA<br>PGKGLEWVSV ISPDSSNTYY ADSVKGRFTI SRDNSKNTLY<br>LQMNSLRAED TAVYYCAKVT GTCGPRSCYY YDAMDVWGQG<br>TLVTVSSGGG GSGGGGSGGG GSQSVLTQPP SASGTPGQRV<br>TISCSGSSSN IGSNAVSWYQ QLPGTAPKLL IYYNSHRPSG<br>VPDRFSGPKS GTSASLAISG LRSEDEADYY CATWDSSLNG<br>YVFGGGTKLT VLG<br>(SEQ ID NO: 146) |

Figure 5:
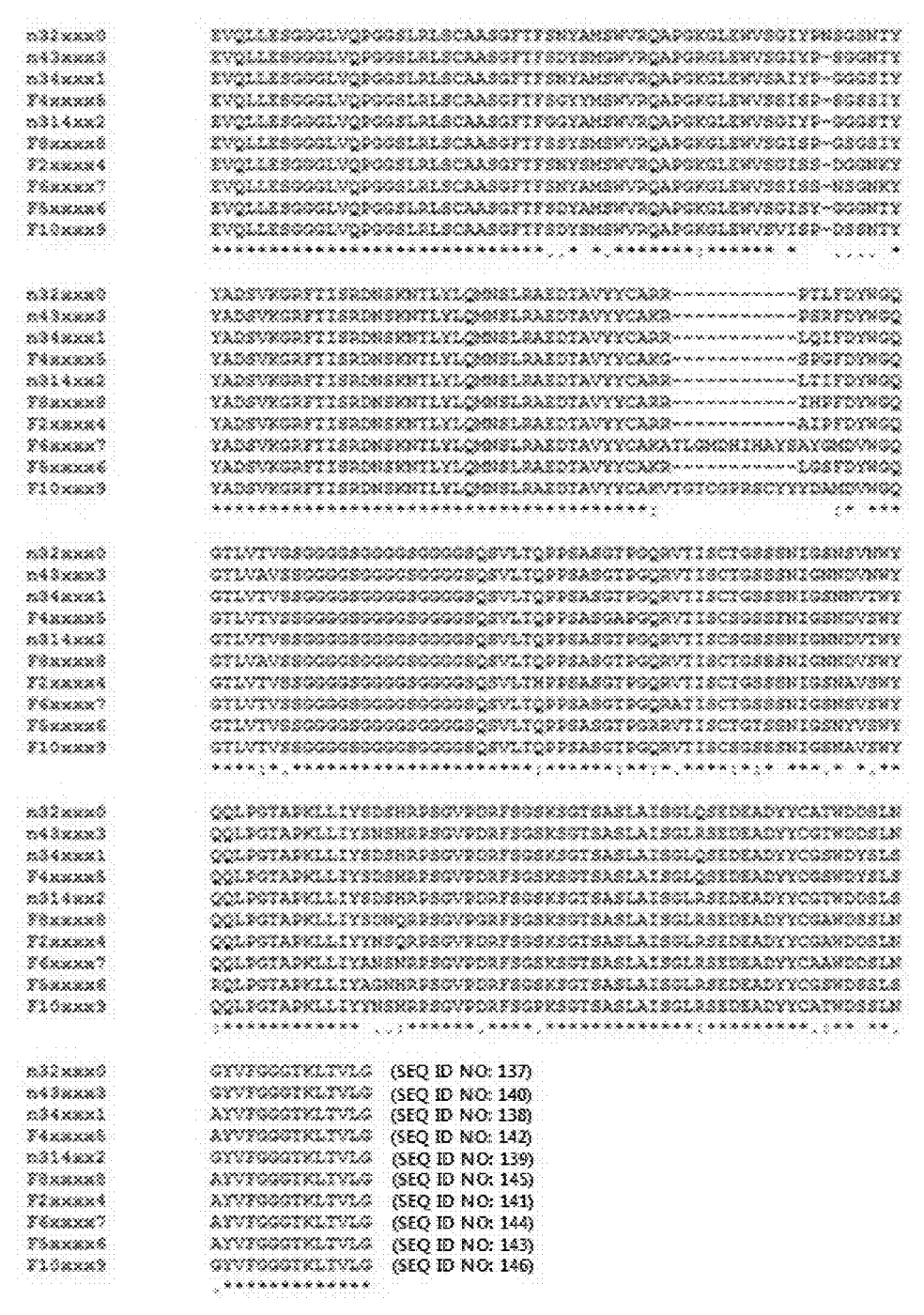

Clone names indicated in FIGS. 3 and 4 corresponding to the antibody names shown in Tables 7 and 8 and FIG. 5 are summarized in Table 9, below:

TABLE 9

| Clone name indicated in FIGS. 3 and 4 | Antibody name indicated in Tables 7 and 8, and FIG. 5 |
|---|---|
| C9 | N32 |
| C10 | N33 |
| C11 | N34 |
| D5 | N36 |
| E9 | N38 |
| G11 | N314 |
| B5 | F5 |
| C5 | F6 |
| E9 | F7 |
| G3 | F8 |

EXAMPLE 3

Expression and Purification of Annexin A1-Binding scFv

Figure 6:
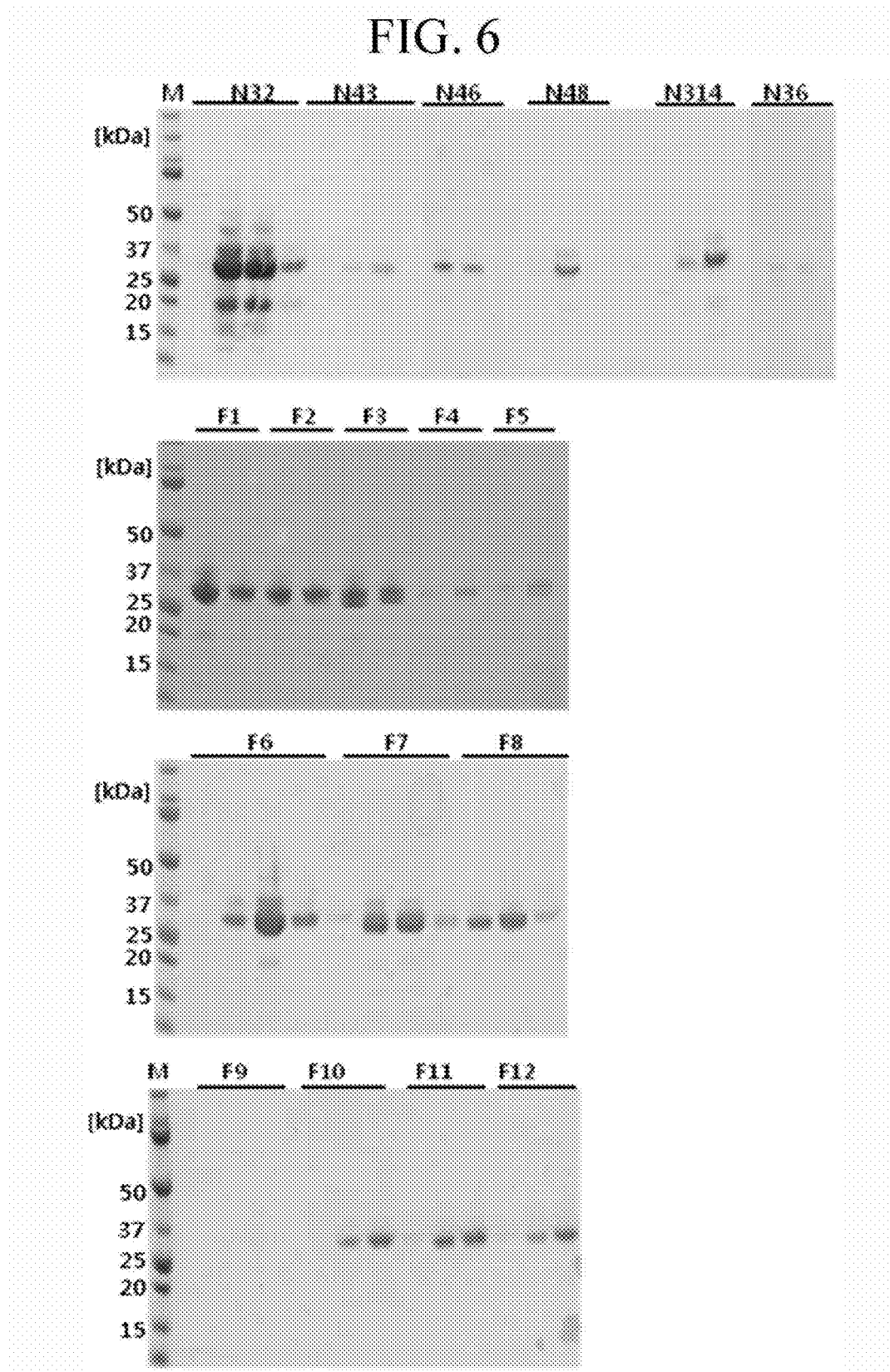
FIG. 6 provides images of SDS-PAGE gels showing sizes and amounts of the Annexin A1-binding scFv proteins purified, as analyzed by SDS-PAGE.

*E. coli* which expresses scFv (N32, N43, N46, N48, N314, N36, F2, F4, F5, F6, F8, F10) specifically binding to Annexin A1 (refer to Example 1) was cultured at 37° C. to optical density at 600 nanometers ($OD_{600}$)=0.6 in an SB broth (30 g bactotryptone, 20 g yeast extract, 10 g MOPS/1 L, Sigma) with shaking, and then was maintained at 30° C. overnight in the presence of 1 mM IPTG (isopropyl-β-D-Thiogalactopyranoside) with shaking, so as to express the antibody. After centrifugation at 8000 rpm, the cell pellet was suspended in 16 ml of a 1×TES buffer (50 mM Tris-HCl, 1 mM EDTA, 20%[w/v] sucrose, pH 8.0), and 30 min later, 24 ml of a 0.2×TES buffer was added to the suspension which was then incubated for 30 min at 4° C. To this, $MgCl_2$ was added at a final concentration of 5 mM, followed by centrifugation at 20000 g for 30 min. The supernatant was allowed to flow through a Ni-NTA column (GE) configured to take advantage of the His-tag expressed together with the scFv antibody. The antibody-bound column was washed with PBS buffer (Gibco) containing 5 mM imidazole (Sigma) to remove unbound proteins. The scFv bound to the Ni-NTA was eluted with PBS buffer containing 300 mM immidazole. The eluted scFv was analyzed for size and quantity by SDS-PAGE. The results are shown in FIG. 6.

EXAMPLE 4

Assay for Binding of Annexin A1-Binding scFv to Extracellular Portion of Annexin A1 in Cancer Cells The selected Annexin A1-binding scFv was analyzed for binding specificity by cell-based ELISA using the cancer cells SNU1 and MDA-MB-231 in which Annexin A1 is overexpressed.

Briefly, after SNU1 (ATCC) and MDA-MB-231 (ATCC) cancer cells were maintained at 37° C. in RPMI-1640 and DMEM, respectively, under a supply of 5% $CO_2$, they were seeded at a density of $5\times10^5$ cells into 96-well plates (NUNC). Purified proteins from the selected scFv (N32, N33, N43, N46, N48, N314, N36, F2, F4, F5, F6, F8, F10) were added in an amount of 250 ng, 125 ng, or 25 ng to each well, incubated at 4° C. for 90 min, and washed twice with HBSS (+) buffer (Gibco, 14025-092; HBSS containing $Ca^{2+}$ and $Mg^{2+}$; calcium chloride ($CaCl_2$) 12.6 mM, magnesium chloride 4.9 mM, and magnesium sulfate 4 mM). Thereafter, a 1/200 dilution of an anti-HA-HRP secondary antibody (Santa Cruz), configured to detect an HA tag conjugated to an scFv terminus, was added to in an amount of 50 ul to each well, and incubated for 1 hr. A color was developed for 10 min with the addition of 150 ul of the Super AquaBlue ELISA substrate solution (eBioScience) for the HRP of the secondary antibody. Absorbance was read at 405 nm to determine the binding of scFv to the Annexin A1 on cancer cells.

Figure 7:
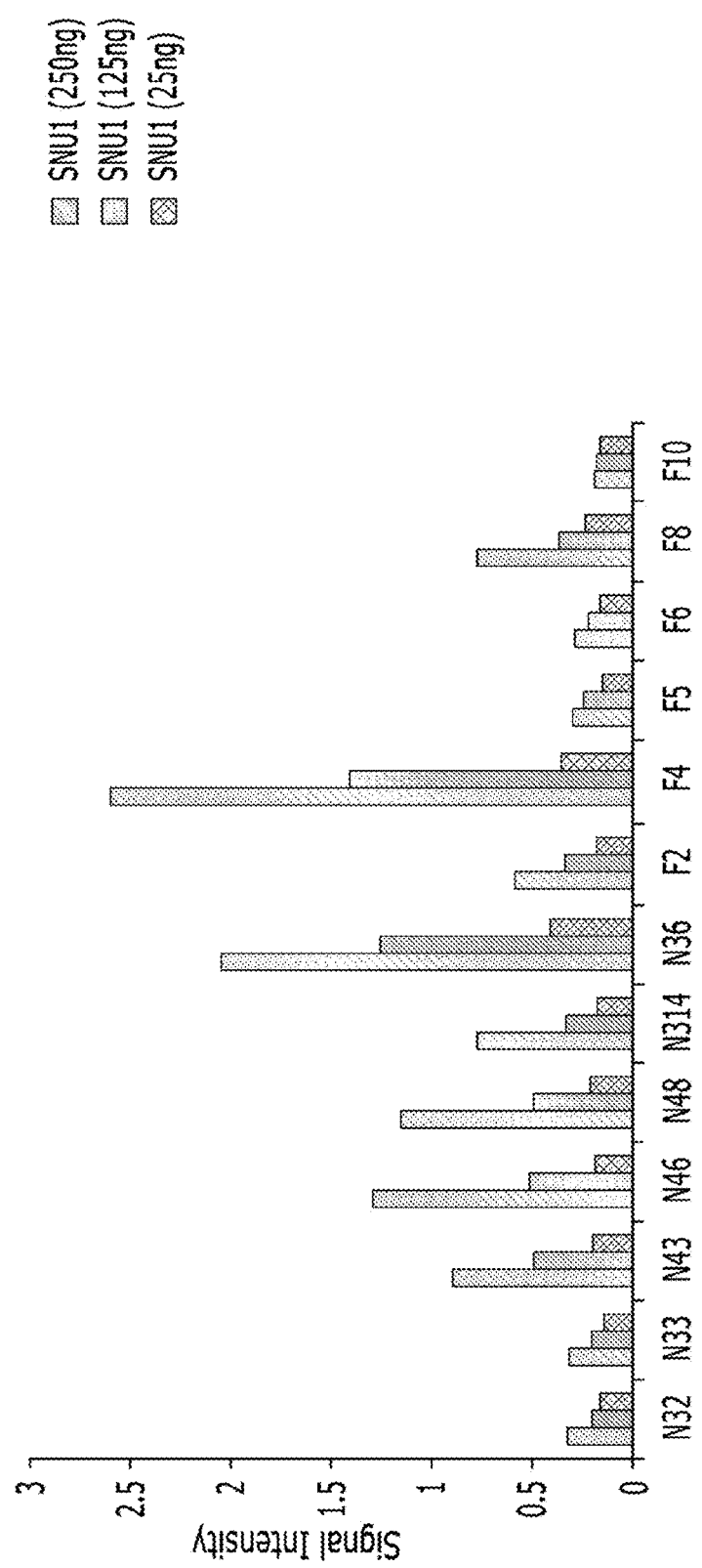
FIG. 7 is a graph showing signal intensities of the Annexin A1-binding scFv selected in SNU1 cells, as measured by cell-based ELISA.
Figure 8:
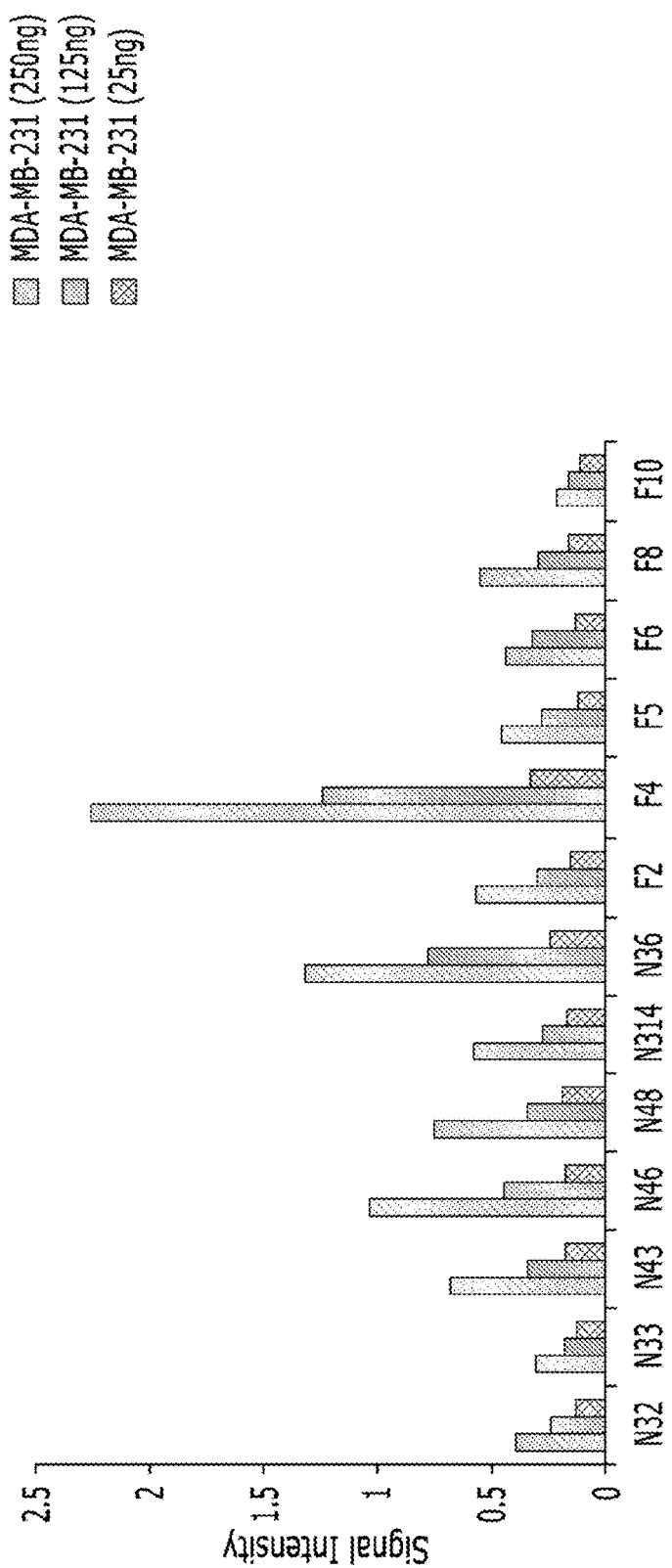
FIG. 8 is a graph showing signal intensities of the Annexin A1-binding scFv selected in MDA-MB-231 cells, as measured by cell-based ELISA.

Data thus obtained are given in FIGS. 7 (SNU1) and 8 (MDA-MB-231). On the Y-axis of FIGS. 7 and 8, signal intensities are represented as numerical values of the absorbance at 405 nm. As can be seen in FIGS. 7 and 8, the binding signal was detected when the scFv screened by biopanning was applied to the cancer cells SNU1 and MDA-MB-231 in which Annexin A1 is overexpressed, and were intensified further with higher concentrations of the scFv, indicating that the scFv specifically binds to Annexin A1 on cancer cells in a dose-dependent manner.

In addition, the screened scFv was assayed for binding specificity for Annexin A1 by FACS in the cancer cells SNU1 and MDA-MB-453 which express Annexin A1 at a high level and a low level, respectively.

Briefly, SNU1 (ATCC) and MDA-MB-453 (negative control; ATCC) cancer cells were grown at 37° C. in RPMI-1640 and DMEM, respectively, under a supply of 5% $CO_2$. The purified scFv N43 was added, and incubated at 4° C. for 30 min. Thereafter, an anti-HA-FITC-conjugated secondary antibody (Santa Cruz), configured to detect an HA tag of an scFv N43 terminus by fluorescence, was added. The FITC fluorescence of the secondary antibody was quantitatively analyzed using the FACScantoii (BD) instrument combined with the Flowjo software so as to determine and quantitate the binding of the scFv to the Annexin A1 on the cancer cell surfaces.

Figure 9:
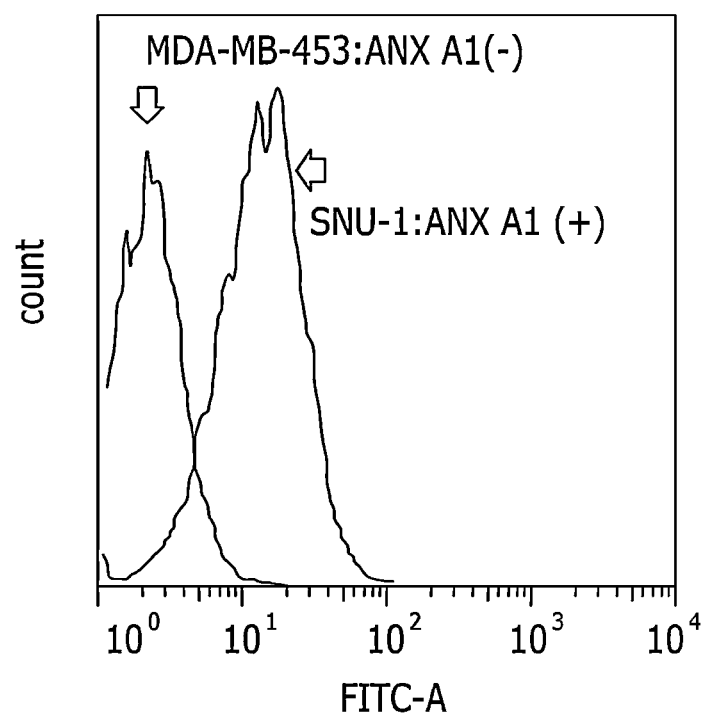
FIG. 9 is a graph showing binding intensities of the Annexin A1-binding scFv selected in SNU1 and MDA-MB-453 (Annexin A1 negative cell), as measured by FACS.

The results are shown in FIG. 9. The Y-axis of FIG. 9 accounts for cell counts according to fluorescence intensity. As in FIG. 8, higher fluorescence intensities were detected from SNU1 in which Annexin A1 is expressed at a higher level, compared to MDA-MB-453 in which Annexin A1 is expressed at a low level, demonstrating that scFv N43 binds to Annexin A1 at levels depending on the expression of Annexin A1.

EXAMPLE 5

Effect of Concentration of the scFv on Binding to Annexin A1 on Cancer Cell Surface Annexin A1-rich SNU-1 (ATCC) and Annexin A1-poor MDA-MB-453 (ATCC) cancer cells were grown at 37° C. in RPMI-1640 and DMEM, respectively, under the supply of 5% $CO_2$ and then incubated at 4° C. for 30 min in the presence of 0.31 ug and 1.25 ug of scFv N43, respectively. Thereafter, a secondary antibody (Santa Cruz), configured to detect an HA tag of an scFv N43 terminus by fluorescence, was added. The FITC fluorescence of the secondary antibody was quantitatively analyzed using the FACScantoii (BD) instrument combined with the Flowjo software so as to quantitate the scFv N43 bound to the cancer cell surfaces.

The results are shown in FIG. 10. The Y-axis of FIG. 10 accounts for cell counts according to fluorescence intensity. As in FIG. 9, the binding intensity increased with an increase in the concentration of scFv N43 in SNU1 which expresses Annexin A1 at a higher level, whereas no clear correlation was observed between the binding intensity and the concentration of scFv N43 in MDA-MB-453 of low Annexin A1 expression. Taken together, the data obtained above indicates that the screened scFv does not bind to cancer cell surfaces in a non-specific manner, but shows specific binding to cancer cell surfaces in a dose-dependent manner.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-Annexin A1 antibody or an antigen-binding fragment thereof comprising:
   a CDR-H1 comprising an amino acid sequence selected from the group consisting of SEQ ID NO: 2 and SEQ ID NO: 147, a CDR-H2 comprising an amino acid sequence selected from the group consisting of SEQ ID NO: 12 to SEQ ID NO: 42, and a CDR-H3 comprising an amino acid sequence selected from the group consisting of SEQ ID NO: 48, SEQ ID NO: 61, SEQ ID NO: 63, SEQ ID NO: 67, SEQ ID NO: 70, SEQ ID NO: 73, and SEQ ID NO: 148; and
   a CDR-L1 comprising an amino acid sequence of SEQ ID NO: 149, a CDR-L2 comprising an amino acid sequence selected from the group consisting of SEQ ID NO: 95 to SEQ ID NO: 112, and a CDR-L3 comprising an amino acid sequence selected from the group consisting of SEQ ID NO: 135 to SEQ ID NO: 150.

2. The anti-Annexin A1 antibody or an antigen-binding fragment thereof of claim 1, comprising:
   a CDR-H1 comprising an amino acid sequence selected from the group consisting of SEQ ID NO: 1 to SEQ ID NO: 11, a CDR-H2 comprising an amino acid sequence selected from the group consisting of SEQ ID NO: 12 to SEQ ID NO: 42, and a CDR-H3 comprising an amino acid sequence selected from the group consisting of SEQ ID NO: 43 to SEQ ID NO: 74; and
   a CDR-L1 comprising an amino acid sequence of SEQ ID NO: 75 to SEQ ID NO: 94, a CDR-L2 comprising an amino acid sequence selected from the group consisting of SEQ ID NO: 95 to SEQ ID NO: 112, and a CDR-L3 comprising an amino acid sequence selected from the group consisting of SEQ ID NO: 113 to SEQ ID NO: 136.

3. The anti-Annexin A1 antibody or an antigen-binding fragment thereof of claim 1, comprising:
   a CDR-H1 comprising an amino acid sequence selected from the group consisting of SEQ ID NO: 1 to SEQ ID NO: 6, a CDR-H2 comprising an amino acid sequence selected from the group consisting of SEQ ID NO: 12 to SEQ ID NO: 26, and a CDR-H3 comprising an amino acid sequence selected from the group consisting of SEQ ID NO: 43 to SEQ ID NO: 57; and
   a CDR-L1 comprising an amino acid sequence of SEQ ID NO: 75 to SEQ ID NO: 85, a CDR-L2 comprising an amino acid sequence selected from the group consisting of SEQ ID NO: 95 to SEQ ID NO: 100, and a CDR-L3 comprising an amino acid sequence selected from the group consisting of SEQ ID NO: 113 to SEQ ID NO: 122.

4. The anti-Annexin A1 antibody or an antigen-binding fragment thereof of claim 1, comprising:
   a CDR-H1 comprising an amino acid sequence selected from the group consisting of SEQ ID NO: 7 to SEQ ID NO: 11, a CDR-H2 comprising an amino acid sequence selected from the group consisting of SEQ ID NO: 27 to SEQ ID NO: 42, and a CDR-H3 comprising an amino acid sequence selected from the group consisting of SEQ ID NO: 58 to SEQ ID NO: 74; and
   a CDR-L1 comprising an amino acid sequence of SEQ ID NO: 86 to SEQ ID NO: 94, a CDR-L2 comprising an amino acid sequence selected from the group consisting of SEQ ID NO: 101 to SEQ ID NO: 112, and a CDR-L3 comprising an amino acid sequence selected from the group consisting of SEQ ID NO: 123 to SEQ ID NO: 136.

5. The anti-Annexin A1 antibody or an antigen-binding fragment thereof of claim 1, comprising an amino acid sequence selected from the group consisting of amino acid sequences of SEQ ID NO: 137 to SEQ ID NO: 146.

6. The anti-Annexin A1 antibody or an antigen-binding fragment thereof of claim 1, wherein the antigen-binding fragment thereof is selected from the group consisting of scFv, (scFv)2, scFv-Fc, Fab, Fab', and F(ab')2.

7. A pharmaceutical composition comprising the anti-Annexin A1 antibody or an antigen-binding fragment thereof of claim 1.

8. The anti-Annexin A1 antibody or an antigen-binding fragment thereof of claim 1, comprising:
   (1) a CDR-H1 comprising SEQ ID NO: 2, a CDR-H2 comprising of SEQ ID NO: 14, a CDR-H3 comprising SEQ ID NO: 54, a CDR-L1 comprising SEQ ID NO: 84, a CDR-L2 comprising SEQ ID NO: 97, and a CDR-L3 comprising SEQ ID NO: 113;
   (2) a CDR-H1 comprising SEQ ID NO: 1, a CDR-H2 comprising of SEQ ID NO: 13, a CDR-H3 comprising SEQ ID NO: 44, a CDR-L1 comprising SEQ ID NO: 76, a CDR-L2 comprising SEQ ID NO: 96, and a CDR-L3 comprising SEQ ID NO: 114;
   (3) a CDR-H1 comprising SEQ ID NO: 2, a CDR-H2 comprising of SEQ ID NO: 14, a CDR-H3 comprising SEQ ID NO: 45, a CDR-L1 comprising SEQ ID NO: 77, a CDR-L2 comprising SEQ ID NO: 97, and a CDR-L3 comprising SEQ ID NO: 113;
   (4) a CDR-H1 comprising SEQ ID NO: 1, a CDR-H2 comprising of SEQ ID NO: 17, a CDR-H3 comprising SEQ ID NO: 48, a CDR-L1 comprising SEQ ID NO: 80, a CDR-L2 comprising SEQ ID NO: 96, and a CDR-L3 comprising SEQ ID NO: 116;
   (5) a CDR-H1 comprising SEQ ID NO: 5, a CDR-H2 comprising of SEQ ID NO: 22, a CDR-H3 comprising SEQ ID NO: 53, a CDR-L1 comprising SEQ ID NO: 83, a CDR-L2 comprising SEQ ID NO: 96, and a CDR-L3 comprising SEQ ID NO: 119;
   (6) a CDR-H1 comprising SEQ ID NO: 6, a CDR-H2 comprising of SEQ ID NO: 25, a CDR-H3 comprising SEQ ID NO: 57, a CDR-L1 comprising SEQ ID NO: 85, a CDR-L2 comprising SEQ ID NO: 96, and a CDR-L3 comprising SEQ ID NO: 121;
   (7) a CDR-H1 comprising SEQ ID NO: 4, a CDR-H2 comprising of SEQ ID NO: 18, a CDR-H3 comprising SEQ ID NO: 49, a CDR-L1 comprising SEQ ID NO: 81, a CDR-L2 comprising SEQ ID NO: 97, and a CDR-L3 comprising SEQ ID NO: 117;

(8) a CDR-H1 comprising SEQ ID NO: 7, a CDR-H2 comprising of SEQ ID NO: 27, a CDR-H3 comprising SEQ ID NO: 58, a CDR-L1 comprising SEQ ID NO: 86, a CDR-L2 comprising SEQ ID NO: 101, and a CDR-L3 comprising SEQ ID NO: 123;
(9 a CDR-H1 comprising SEQ ID NO: 8, a CDR-H2 comprising of SEQ ID NO: 28, a CDR-H3 comprising SEQ ID NO: 59, a CDR-L1 comprising SEQ ID NO: 87, a CDR-L2 comprising SEQ ID NO: 96, and a CDR-L3 comprising SEQ ID NO: 115;
(10) a CDR-H1 comprising SEQ ID NO: 4, a CDR-H2 comprising of SEQ ID NO: 29, a CDR-H3 comprising SEQ ID NO: 60, a CDR-L1 comprising SEQ ID NO: 88, a CDR-L2 comprising SEQ ID NO: 102, and a CDR-L3 comprising SEQ ID NO: 124;
(11) a CDR-H1 comprising SEQ ID NO: 1, a CDR-H2 comprising of SEQ ID NO: 30, a CDR-H3 comprising SEQ ID NO: 61, a CDR-L1 comprising SEQ ID NO: 82, a CDR-L2 comprising SEQ ID NO: 103, and a CDR-L3 comprising SEQ ID NO: 125;
(12) a CDR-H1 comprising SEQ ID NO: 9, a CDR-H2 comprising of SEQ ID NO: 31, a CDR-H3 comprising SEQ ID NO: 62, a CDR-L1 comprising SEQ ID NO: 89, a CDR-L2 comprising SEQ ID NO: 104, and a CDR-L3 comprising SEQ ID NO: 126; or
(13) a CDR-H1 comprising SEQ ID NO: 10, a CDR-H2 comprising of SEQ ID NO: 32, a CDR-H3 comprising SEQ ID NO: 63, a CDR-L1 comprising SEQ ID NO: 90, a CDR-L2 comprising SEQ ID NO: 105, and a CDR-L3 comprising SEQ ID NO: 127.

* * * * *